United States Patent
Harada et al.

(10) Patent No.: US 10,793,524 B2
(45) Date of Patent: Oct. 6, 2020

(54) METHOD FOR PRODUCING AROMATIC NITRILE COMPOUND AND METHOD FOR PRODUCING CARBONIC ACID ESTER

(71) Applicant: MITSUBISHI GAS CHEMICAL COMPANY, INC., Tokyo (JP)

(72) Inventors: Hidefumi Harada, Tokyo (JP); Yousuke Shinkai, Tokyo (JP); Hongyu Liu, Tokyo (JP); Takehiko Isobe, Tokyo (JP); Yoshinori Isahaya, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 16/470,817

(22) PCT Filed: Nov. 30, 2017

(86) PCT No.: PCT/JP2017/042936
§ 371 (c)(1),
(2) Date: Jun. 18, 2019

(87) PCT Pub. No.: WO2018/116775
PCT Pub. Date: Jun. 28, 2018

(65) Prior Publication Data
US 2019/0382345 A1    Dec. 19, 2019

(30) Foreign Application Priority Data

Dec. 21, 2016 (JP) ................................. 2016-248094

(51) Int. Cl.
| | |
|---|---|
| *C07D 213/84* | (2006.01) |
| *B01J 23/04* | (2006.01) |
| *B01J 37/02* | (2006.01) |
| *B01J 37/08* | (2006.01) |
| *C07D 213/82* | (2006.01) |

(52) U.S. Cl.
CPC .......... *C07D 213/84* (2013.01); *B01J 23/04* (2013.01); *B01J 37/0213* (2013.01); *B01J 37/0236* (2013.01); *B01J 37/08* (2013.01); *C07D 213/82* (2013.01)

(58) Field of Classification Search
CPC .................................................. C07D 213/84
USPC .......................................................... 546/323
See application file for complete search history.

(56) References Cited

U.S. PATENT DOCUMENTS 6,320,067 B1    11/2001   Oku et al.

FOREIGN PATENT DOCUMENTS

| EP | 1057807 | 12/2000 |
|---|---|---|
| JP | 7-145130 | 6/1995 |
| JP | 2000-344723 | 12/2000 |
| JP | 2003-252845 | 9/2003 |
| JP | 2005-194224 | 7/2005 |
| JP | 2009-184934 | 8/2009 |
| JP | 2009-213975 | 9/2009 |
| JP | 2010-77113 | 4/2010 |
| JP | 2012-162523 | 8/2012 |
| WO | 2009/137742 A1 | 11/2009 |
| WO | 2015/099053 | 7/2015 |

OTHER PUBLICATIONS

Campbell, J.A. et al., "Laboratory-Scale Synthesis of Nitriles by Catalysed Dehydration of Amides and Oximes under Flash Vacuum Pyrolysis (FVP) Conditions, (20)", Synthesis, 2007, pp. 3179-3184.
Joshi, G.W. et al., "Dehydration of carboxamides to nitriles with zirconia catalyst, 24", Chemistry and Industry, 1986, pp. 876-877.
Official Communication in International Application No. PCT/JP2017/042936, dated Feb. 27, 2018.
Extended European search report dated Oct. 14, 2019 in EP patent application No. 17882571.7.
Honda Masayoshi et al: Journal of Catalysis, Academic Press, Duluth, MN, US, vol. 318, Aug. 17, 2014 (Aug. 17, 2014) pp. 95-107.

*Primary Examiner* — Taofiq A Solola
(74) *Attorney, Agent, or Firm* — Greenblum & Bernstein, P.L.C.

(57) ABSTRACT

Provided is a method for regenerating an aromatic amide compound into a corresponding aromatic nitrile compound, the method realizing a dehydration reaction of providing a target compound selectively at a high yield, with generation of a by-product being suppressed. Also provided is a method for producing an aromatic nitrile compound that decreases the number of steps of the dehydration reaction and significantly improves the reaction speed even at a pressure close to normal pressure. In addition, the above-described production method is applied to a carbonate ester production method to provide a method for producing a carbonate ester efficiently. The above-described methods are realized by a method for producing an aromatic nitrile compound including a dehydration reaction of dehydrating an aromatic amide compound, in which the dehydration reaction uses, as a solvent, any of 1,2-dimethoxybenzene, 1,3-dimethoxybenzene and 1,3,5-trimethoxybenzene.

22 Claims, 3 Drawing Sheets

METHOD FOR PRODUCING AROMATIC NITRILE COMPOUND AND METHOD FOR PRODUCING CARBONIC ACID ESTER

TECHNICAL FIELD

The present invention relates to a method for producing an aromatic nitrile compound such as cyanopyridine or the like, and a method for producing a carbonate ester.

BACKGROUND ART

"Carbonate ester" is a generic name of a compound obtained as a result of one atom or two atoms among two hydrogen atoms of carbonic acid, $CO(OH)_2$, being substituted with an alkyl group or an aryl group, and has a structure of RO—C(=O)—OR' (R and R' each represent a saturated hydrocarbon group or an unsaturated hydrocarbon group).

A carbonate ester is used as an additive, for example, a gasoline additive for improving the octane value and a diesel fuel additive for decreasing the amount of particles in exhaust gas. A carbonate ester is also used as, for example, an alkylation agent, a carbonylation agent, a solvent or the like for synthesizing resins or organic compounds such as polycarbonate, urethane, pharmaceutical drugs, agricultural chemicals or the like, a material of an electrolytic solution of lithium ion cells, a material of lubricant oil, or a material of an oxygen absorber for rust inhibition of boiler pipes. As can be seen, a carbonate ester is a very useful compound.

According to a conventionally mainstream method for producing a carbonate ester, phosgene, which is used as a source of a carbonyl, is directly reacted with an alcohol. Phosgene used in this method is highly hazardous and highly corrosive, and therefore, needs extreme caution when being handled, for example, transported or stored. It is highly costly to control and manage, and guarantee the safety of, production facilities of phosgene. According to this method, the materials and catalysts used for producing a carbonate ester contain halogen such as chlorine or the like, and the produced carbonate ester contains a trace amount of halogen, which is not removed by a simple purification step. When the carbonate ester is used for a gasoline additive, a light oil additive or an electronic material, such halogen may undesirably cause corrosion. Therefore, a thorough purification step is indispensable to decrease the trace amount of halogen present in the carbonate ester to the level of an extremely trace amount. In addition, recently, administrative offices provide a strict administration guidance and do not permit new establishment of production facilities using this method because this method uses phosgene, which is highly hazardous to the human body. In such a situation, a new production method of a carbonate ester that does not use phosgene is strongly desired.

There is another known method for producing a carbonate ester. According to this method, a carbonate ester is directly synthesized from an alcohol and carbon dioxide using a heterogeneous catalyst. Regarding this method, studies had been made on using 2-cyanopyridine or benzonitrile as a wettable powder to significantly improve the production amount and the production speed of the carbonate ester, to allow the reaction to advance easily at a pressure close to normal pressure, and to increase the reaction speed (see Patent Documents 1 and 2). However, there was a problem regarding the method for treating or using benzamide or the like generated as a by-product.

For example, benzamide generated by the reaction of benzonitrile and water is limited to being usable for some of pharmaceutical and agrochemical intermediates. Therefore, regarding the method of producing a carbonate ester using benzonitrile as a wettable powder, benzamide generated as a by-product is desired to be regenerated into benzonitrile and reused. It is now an issue to realize a regeneration reaction with a high level of selectivity (because it is considered that if a by-product is generated, benzonitrile is not easily used as a wettable powder) and a high yield (because if the yield is low, benzamide remains in a large amount, which increases the amount of work, namely, work load, of separating benzamide and benzonitrile from each other).

In light of the above-described situation where regeneration of benzamide or the like into benzonitrile or the like involves problems, there is a known method for realizing the regeneration with no use of a strong reagent and with the generation of a by-product being suppressed (Patent Document 3).

However, according to this method, generation of nitrile by dehydration of an amide compound requires 400 hours and thus is not well balanced with, namely, is not usable together with, a carbonate ester synthesis reaction, which requires only 24 hours. This method also has a problem that steps of extraction, infiltration and the like are necessary for solid-liquid separation of a catalyst, which increases the number of production steps and complicates the production process.

CITATION LIST

Patent Literature

Patent Document 1: Japanese Laid-Open Patent Publication No. 2010-77113
Patent Document 2: Japanese Laid-Open Patent Publication No. 2012-162523
Patent Document 3: WO2015/099053

SUMMARY OF INVENTION

Technical Problem

In light of the above-described technological problems, an object of the present invention is to provide a method for regenerating an aromatic amide compound, for example, pyridine carboamide, into a corresponding aromatic nitrile compound, namely, cyanopyridine, the method realizing a dehydration reaction of providing a target compound selectively at a high yield, with generation of a by-product being suppressed. Another object of the present invention is to provide a method for producing an aromatic nitrile compound that decreases the number of steps of the dehydration reaction and significantly improves the reaction speed to shorten the reaction time even at a pressure close to normal pressure.

A still another object of the present invention is to apply the above-described method for producing an aromatic nitrile compound to a carbonate ester production method to provide a method for producing a carbonate ester efficiently.

Solution to Problem

In order to achieve the above-described objects, the present inventors made studies on a method for producing an aromatic nitrile compound such as cyanopyridine or the like by dehydration of an aromatic amide compound. More specifically, the present inventors studied reaction conditions for dehydrating an aromatic amide compound, and as a result, found the following. In the case where a predetermined solvent is used, a process of dehydration reaction is realized by which the reaction speed is significantly improved to shorten the reaction time, the target compound is obtained selectively at a high yield while generation of a by-product is suppressed, and the aromatic nitrile compound is easily recovered. The present inventors also found the following. Since the process of dehydration reaction conceived by the present inventors does not need solid-liquid separation of a catalyst, the number of steps of the dehydration reaction is decreased. Preferably, the dehydration reaction is advanced in a state where the solvent is boiled.

By the present invention described above, the speed of regenerating an aromatic nitrile compound by a dehydration reaction of an aromatic amide compound, and the speed of synthesizing a carbonate ester from $CO_2$ and an alcohol using the aromatic nitrile compound, are now well balanced. Namely, the dehydration reaction and the carbonate ester synthesis reaction are now established as a series of commercial processes. Based on this, the present inventors also made studies on applying the above-described knowledge to a method for producing a carbonate ester. Namely, the present inventors have found the following regarding the carbonate ester production method of directly synthesizing a carbonate ester from an alcohol and carbon dioxide. In the case where, for example, a solvent having a boiling point higher than that of the aromatic amide compound is used, the number of steps of the reaction is decreased and the method is simplified with no need of solid-liquid separation of a catalyst. The present inventors have confirmed that such a carbon ester synthesis method may be combined with the dehydration reaction, using a predetermined solvent, of an aromatic amide compound to generate an aromatic nitrile compound, so that a splendid effect is provided. The gist of the present invention is as follows.

(1) A method for producing an aromatic nitrile compound, comprising:

a dehydration reaction of dehydrating an aromatic amide compound;

wherein the dehydration reaction uses a solvent containing one or a plurality of substances selected from 1,2-dimethoxybenzene, 1,3-dimethoxybenzene and 1,3,5-trimethoxybenzene.

(2) The method for producing an aromatic nitrile compound according to (1) above, wherein a total amount of the one or the plurality of substances selected from 1,2-dimethoxybenzene, 1,3-dimethoxybenzene and 1,3,5-trimethoxybenzene is 5% by weight or greater with respect to the solvent.

(3) The method for producing an aromatic nitrile compound according to (1) or (2) above, wherein the solvent is formed of only the one or the plurality of substances selected from 1,2-dimethoxybenzene, 1,3-dimethoxybenzene and 1,3,5-trimethoxybenzene.

(4) The method for producing an aromatic nitrile compound according to (1) or (2) above, wherein the solvent is a mixed solvent further containing a compound having a boiling point that is higher than the boiling point of the aromatic nitrile compound and the boiling point of water and is lower than the boiling point of the aromatic amide compound.

(5) The method for producing an aromatic nitrile compound according to any one of (1) through (4) above, wherein the solvent is used in an amount larger than, or equal to, an equimolecular amount of the aromatic amide compound.

(6) The method for producing an aromatic nitrile compound according to any one of (1) through (5) above, wherein the dehydration reaction is performed in a state where the solvent is boiled.

(7) The method for producing an aromatic nitrile compound according to any one of (1) through (6) above, wherein the dehydration reaction is performed under the condition of normal pressure or a reduced pressure.

(8) The method for producing an aromatic nitrile compound according to any one of (1) through (7) above, wherein a reaction solution of the dehydration reaction has a temperature of 170° C. or higher and lower than 230° C.

(9) The method for producing an aromatic nitrile compound according to any one of (1) through (8) above, wherein the aromatic amide compound contains pyridine carboamide, and the aromatic nitrile compound contains cyanopyridine.

(10) The method for producing an aromatic nitrile compound according to any one of (1) through (9) above, wherein the dehydration reaction uses a catalyst containing cesium.

(11) A method for producing an aromatic nitrile compound, comprising:

a dehydration reaction of dehydrating an aromatic amide compound;

wherein the dehydration reaction uses a solvent containing one or a plurality of substances selected from 1,2,3,4-tetrahydronaphthalene, 1,2-dimethoxybenzene, 1,3-dimethoxybenzene and 1,3,5-trimethoxybenzene, and a catalyst containing cesium.

(12) A method for producing a carbonate ester, comprising:

a first reaction step including a carbonate ester generation reaction of reacting an alcohol and carbon dioxide in the presence of an aromatic nitrile compound to generate a carbonate ester and water, and a hydration reaction of hydrating the aromatic nitrile compound with the generated water to generate an aromatic amide compound; and a second reaction step of, after the aromatic amide compound is separated from a reaction system of the first reaction step, regenerating the aromatic amide compound into an aromatic nitrile compound by a dehydration reaction of dehydrating the aromatic amide compound in a solvent containing one or a plurality of substances selected from 1,2-dimethoxybenzene, 1,3-dimethoxybenzene and 1,3,5-trimethoxybenzene;

wherein at least a part of the aromatic nitrile compound regenerated in the second reaction step is used in the first reaction step.

(13) The method for producing a carbonate ester according to (12) above, wherein a total amount of the one or the plurality of substances selected from 1,2-dimethoxybenzene, 1,3-dimethoxybenzene and 1,3,5-trimethoxybenzene is 5% by weight or greater with respect to the solvent.

(14) The method for producing an aromatic nitrile compound according to (12) or (13) above, wherein the solvent is formed of only the one or the plurality of substances selected from 1,2-dimethoxybenzene, 1,3-dimethoxybenzene and 1,3,5-trimethoxybenzene.

(15) The method for producing a carbonate ester according to (12) or (13) above, wherein the solvent is a mixed solvent further containing a compound having a boiling point that is higher than the boiling point of the aromatic nitrile compound and the boiling point of water and is lower than the boiling point of the aromatic amide compound.

(16) The method for producing a carbonate ester according to any one of (12) through (15) above, wherein the solvent is used in an amount larger than, or equal to, an equimolecular amount of the aromatic amide compound.

(17) The method for producing a carbonate ester according to any one of (12) through (16) above, wherein the dehydration reaction is performed in a state where the solvent is boiled.

(18) The method for producing a carbonate ester according to any one of (12) through (17) above, wherein the dehydration reaction is performed under the condition of normal pressure or a reduced pressure.

(19) The method for producing a carbonate ester according to any one of (12) through (18) above, wherein a reaction solution of the dehydration reaction has a temperature of 170° C. or higher and lower than 230° C.

(20) The method for producing a carbonate ester according to any one of (12) through (19) above, wherein the aromatic amide compound contains pyridine carboamide, and the aromatic nitrile compound contains cyanopyridine.

(21) The method for producing a carbonate ester according to any one of (12) through (20) above, wherein the dehydration reaction uses a catalyst containing cesium.

(22) The method for producing a carbonate ester according to any one of (12) through (21) above, wherein the carbonate ester generation reaction uses a catalyst containing cerium.

(23) The method for producing a carbonate ester according to any one of (12) through (22) above, wherein the alcohol contains an alcohol having a carbon number of 1 through 6.

(24) A method for producing a carbonate ester, comprising:

a first reaction step including a carbonate ester generation reaction of reacting an alcohol and carbon dioxide in the presence of an aromatic nitrile compound to generate a carbonate ester and water, and a hydration reaction of hydrating the aromatic nitrile compound with the generated water to generate an aromatic amide compound; and a second reaction step of, after the aromatic amide compound is separated from a reaction system of the first reaction step, regenerating the aromatic amide compound into an aromatic nitrile compound by a dehydration reaction of dehydrating the aromatic amide compound in a solvent containing one or a plurality of substances selected from 1,2,3,4-tetrahydronaphthalene, 1,2-dimethoxybenzene, 1,3-dimethoxybenzene and 1,3,5-trimethoxybenzene by use of a catalyst containing cesium;

wherein at least a part of the aromatic nitrile compound regenerated in the second reaction step is used in the first reaction step.

(25) A method for producing a carbonate ester, comprising:

a first reaction step including a carbonate ester generation reaction of reacting an alcohol and carbon dioxide in the presence of an aromatic nitrile compound to generate a carbonate ester and water, and a hydration reaction of hydrating the aromatic nitrile compound with the generated water to generate an aromatic amide compound; and a second reaction step of, after the aromatic amide compound is separated from a reaction system of the first reaction step, regenerating the aromatic amide compound into an aromatic nitrile compound by a dehydration reaction of dehydrating the aromatic amide compound in a solvent formed of only one or a plurality of substances selected from 1,2,3,4-tetrahydronaphthalene, 1,2-dimethoxybenzene, 1,3-dimethoxybenzene and 1,3,5-trimethoxybenzene by use of a catalyst containing cesium;

wherein at least a part of the aromatic nitrile compound regenerated in the second reaction step is used in the first reaction step.

Advantageous Effects of Invention

According to the present invention as described above, an aromatic nitrile compound such as cyanopyridine or the like is efficiently produced (regenerated) from an aromatic amide compound such as pyridine carbonamide (picolinamide, nicotinamide or the like), benzamide or the like. More specifically, the dehydration reaction of an aromatic amide compound for the regeneration is performed to obtain a target compound selectively at a high yield, while generation of a by-product is suppressed. Even under mild reaction conditions, for example, at a pressure close to normal pressure, the reaction speed is increased. Therefore, according to the present invention, the reaction time of the dehydration reaction of regenerating an aromatic nitrile compound is significantly shortened as compared with the reaction time required by the conventional method.

Also according to the present invention, an aromatic nitrile compound is produced as described above, and as a result, a method for producing a carbonate ester efficiently is realized.

DESCRIPTION OF EMBODIMENTS

Figure 1:
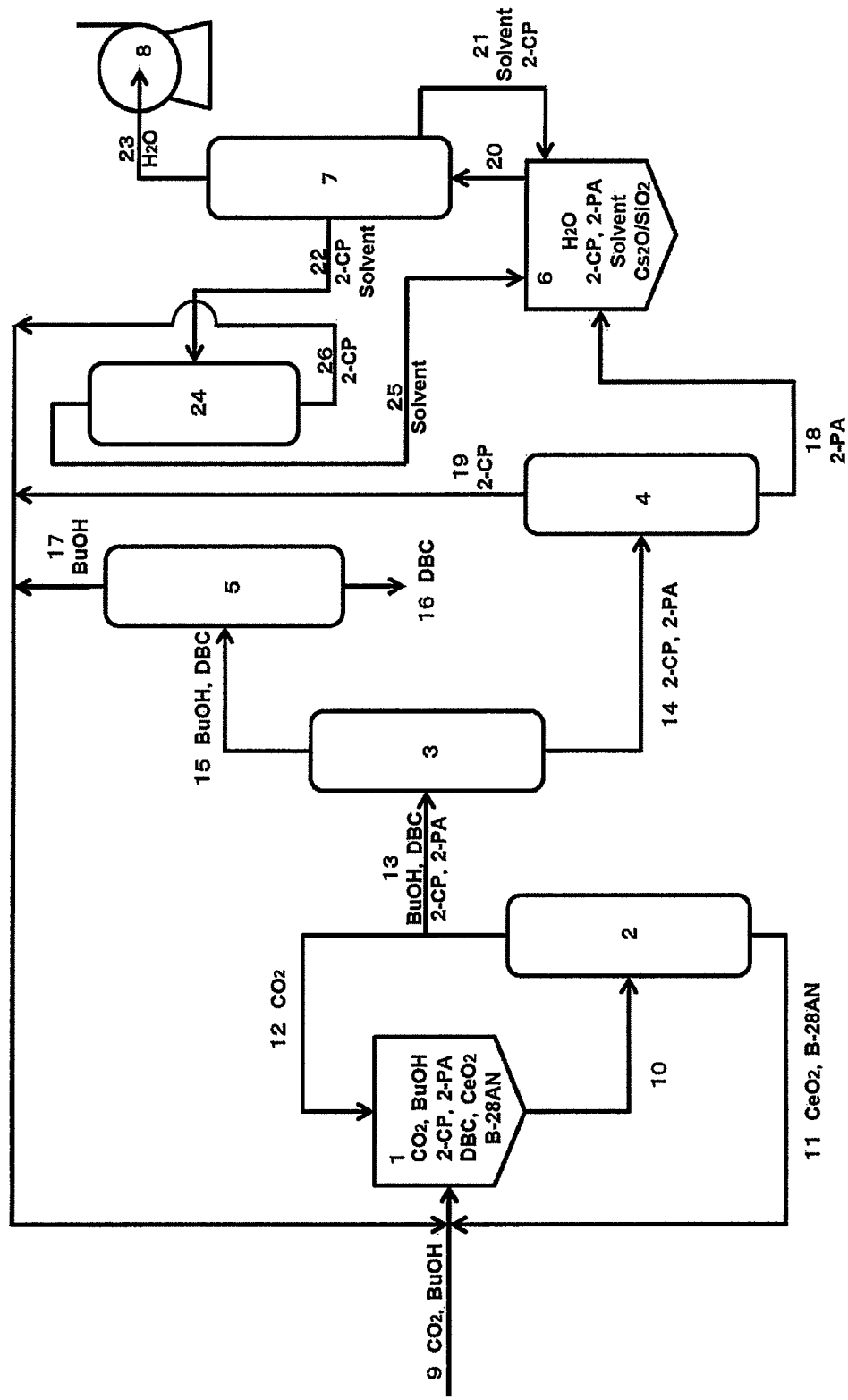
FIG. 1 shows an example of device for producing a carbonate ester.

Hereinafter, a preferable embodiment of the present invention will be described in detail with reference to the attached drawings. In the specification and the drawings, components having substantially the same functions or structures will bear the same reference signs, and the same descriptions will not be repeated.

<1. Method for Producing an Aromatic Nitrile Compound>

According to a method of the present invention for producing an aromatic nitrile compound, an aromatic nitrile compound such as cyanopyridine or the like is produced by dehydration of an aromatic amide compound such as pyridine carboamide (2-pyridine carboamide, 3-pyridine carboamide or 4-pyridine carboamide) or the like. According to this method, an aromatic amide compound is subjected to a dehydration reaction in the presence of, for example, a catalyst containing a carried basic metal oxide and a predetermined solvent to generate an aromatic nitrile compound.

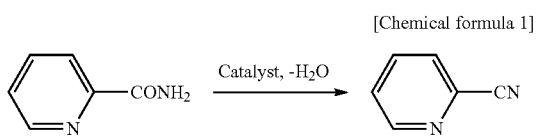 [SMILES: NC(=O)c1ccccn1 ; N#Cc1ccccn1]

[Chemical formula 1]

(Catalyst)

The catalyst usable in the above-described dehydration reaction according to the present invention contains an oxide of an alkaline metal (K, Li, Na, Rb, Cs), which is basic. It is especially preferable that the catalyst usable in the above-described reaction contains an oxide of at least one of Na, K, Rb and Cs (cesium). A carrier of the catalyst may be a substance that generally acts as a carrier of a catalyst. As a result of studies made on various carriers, it has been found that a catalyst containing one or two of $SiO_2$ and $ZrO_2$ as a carrier exhibits an especially high level of performance.

Examples of methods for producing a catalyst usable for the above-described dehydration reaction will be described. In the case where the carrier is $SiO_2$, commercially available powdery or spherical $SiO_2$ is usable. Preferably, $SiO_2$ is sized to 100 mesh (0.15 mm) or less so that an active metal is uniformly carried, and is pre-baked at 700° C. for 1 hour in the air in order to remove the moisture. There are various types of $SiO_2$ of various properties. $SiO_2$ having a larger surface area is more preferable because as the surface area is larger, the active metal is dispersed more highly and the generation amount of an aromatic nitrile compound is increased. Specifically, a surface area of 300 $m^2$ or greater is preferable. It should be noted that there may be a case where the surface area of the prepared catalyst is smaller than the surface area of $SiO_2$ alone as a result of, for example, mutual action of $SiO_2$ and the active metal. In this case, the surface area of the produced catalyst is preferably 150 $m^2$ or greater. The metal oxide acting as an active species may be carried by an impregnation method such as an incipient wetness method, an evaporation-to-dryness method or the like.

A metal salt acting as a precursor of the catalyst merely needs to be water-soluble. Examples of usable alkaline metal salts include various compounds such as carbonate, hydrogencarbonate, chloride, nitrate, silicate and the like. An aqueous solution of a precursor formed of a basic metal is impregnated with a carrier, then is dried and baked. The resultant substance is usable as a catalyst. The baking temperature, which depends on the precursor used, is preferably 400 to 600° C.

The amount of the catalyst to be carried may be set appropriately. For example, the amount of an alkaline metal oxide to be carried, converted to the metal, is set to preferably about 0.1 to 1.5 mmol/g, and especially preferably about 0.1 to 1 mmol/g, with respect to the total weight of the catalyst. In the case where the amount to be carried is larger than such a value, the activity may undesirably be decreased. The amount of the catalyst to be used for the reaction may be set appropriately.

A catalyst preferably usable in the present invention includes a carrier formed of one or two of $SiO_2$ and $ZrO_2$ and only an alkaline metal oxide(s) of one, or at least two, types carried by the carrier. The catalyst may contain, in addition to the above-described elements, unavoidable impurities incorporated in a step of, for example, producing the catalyst. Nonetheless, it is desirable to avoid incorporation of impurities to a maximum possible degree.

The catalyst, usable in the present invention, including a metal oxide acting as an active species and carried by the carrier may be in the form of powder or a molded body. In the case of being a molded body, the catalyst may be spherical, pellet-like, cylindrical, ring-shaped, wheel-shaped, granular or the like.

(Reaction Format and Reaction Vessel)

With the method according to the present invention for producing an aromatic nitrile compound using the catalyst, there is no specific limitation on the form of the reaction. A flow reactor such as a batch reactor, a semi-batch reactor, a continuous tank reactor, a tube reactor or the like is usable. For the catalyst, a fixed bed, a slurry bed or the like is usable.

With the method for producing an aromatic nitrile compound according to the present invention, it is desirable to perform the reaction to produce an aromatic nitrile compound while removing by-product water generated by the dehydration reaction. For example, it is desirable to perform reflux or distillation or to provide a dehydration agent such as zeolite or the like in the system, so that the reaction is performed while the by-product water is removed. As a result of the active studies made by the present inventors, it has been found that the generation amount of an aromatic nitrile compound may be increased as follows by use of, for example, a reaction distillation device having a decompression device attached thereto. A catalyst, an aromatic amide compound and a solvent are put into a reaction tube, the pressure is reduced to control the temperature of the reaction solution, and the solvent is refluxed to distill the reaction liquid to separate and remove the by-product water from the system.

(Solvent)

A solvent usable for the above-described dehydration reaction contains one or a plurality of substances selected from 1,2-dimethoxybenzene, 1,3-dimethoxybenzene and 1,3,5-trimethoxybenzene. In addition to the above-listed three substances, 1,2,3,4-tetrahydronaphthalene may be included in a list of usable solvents. In the dehydration reaction using a solvent containing one or a plurality of substances selected from 1,2,3,4-tetrahydronaphthalene, 1,2-dimethoxybenzene, 1,3-dimethoxybenzene and 1,3,5-trimethoxybenzene as described above, it is preferable to use a catalyst containing cesium. For the dehydration reaction, it is preferable to use a solvent formed only of one or a plurality of above-listed substances, namely, 1,2,3,4-tetrahydronaphthalene, 1,2-dimethoxybenzene, 1,3-dimethoxybenzene and 1,3,5-trimethoxybenzene (hereinafter, these four substances will each be referred to as a "specific solvent compound). Alternatively, a mixed solvent containing another compound is also usable.

The mixed solvent usable for the dehydration reaction may contain another compound in addition to any of the four specific solvent compounds listed above or any of the three specific solvent compounds listed above other than 1,2,3,4-tetrahydronaphthalene. In the case where the mixed solvent contains a compound other than the specific solvent compounds, it is especially preferable that the compound has a boiling point that is higher than the boiling point of the aromatic nitrile compound to be produced (regenerated) and also the boiling point of water and is lower than the boiling point of the aromatic amide compound to be dehydrated. The compound contained in the mixed solvent as a compound other than the specific solvent compounds is, for example, diphenylether. Diphenylether has a high boiling point of about 259° C. and suppresses the evaporation amount of the mixed solvent containing the specific solvent compound(s), and thus advances the dehydration reaction efficiently. Therefore, diphenylether is preferably usable.

Figure 3:
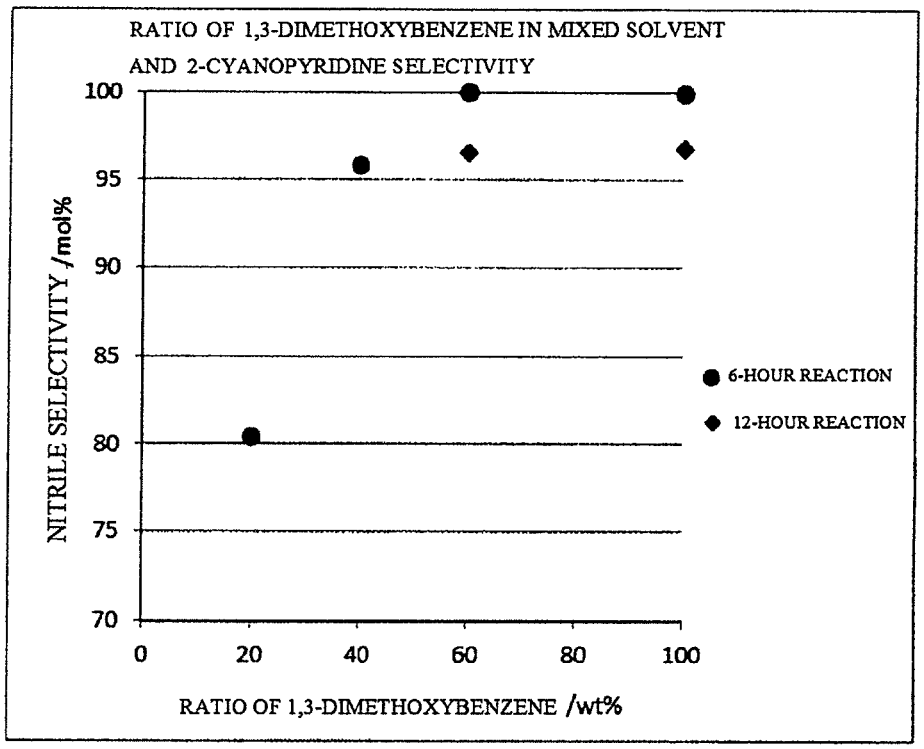
FIG. 3 is a graph showing the composition of the solvents in the mixed solvent and the nitrile selectivity (ratio of the amount of the aromatic nitrile compound and the total amount of impurities).

With respect to the mixed solvent used for the dehydration reaction, the total amount of the four specific solvent compounds (or the three specific solvent compounds other than 1,2,3,4-tetrahydronaphthalene) is preferably 5% by weight or greater, more preferably 20% by weight or greater, and especially preferably 40% by weight or greater. In the case where the total amount of the specific solvent compounds is adjusted to be within such a range, the selectivity (mol %) of the aromatic nitrile compound represented by expression (1) below (ratio of the amount of the generated aromatic nitrile compound with respect to the amount of the reacted aromatic amide compound; hereinafter, this selectivity will also be referred to as "nitrile selectivity"; regarding the details, refer to FIG. 3 described below) is improved while another compound having a preferable property such as, for example, a preferable boiling point is allowed to be contained in the solvent.

[Expression 1]

Amount of aromatic nitrile compound (mol)/(amount of pre-reaction aromatic amide compound (mol)−amount of post-reaction aromatic amide compound (mol))×100     expression 1

The amount of the solvent to be used for the dehydration reaction is, for example, greater than, or equal to, the equimolecular amount of the aromatic amide compound, which is the target of the dehydration reaction. If the amount of the solvent to be used is too small, the speed of the dehydration reaction is decreased to increase the amount of by-products. Therefore, the amount of the solvent to be used for the dehydration reaction is preferably five times the molar amount, more preferably 15 times the molar amount, and especially preferably 25 times the molar amount, of the aromatic amide compound.

(Conditions for the Dehydration Reaction)

It is preferable that the reaction conditions are selected from the points of view of the dehydration reaction speed, the boiling point of the solvent, the by-product generated by the reaction such as pyridine or the like, the economic efficiency and the like. In the case where a mixed solvent is used in the dehydration reaction, it is difficult to accurately define and measure the boiling point of the solvent. It is generally preferable that the boiling point of the mixed solvent is higher than the boiling point of the aromatic nitrile compound and the boiling point of water and is lower than the boiling point of the aromatic amide compound. In the case where a mixed solvent having a boiling point in such a range is used in the dehydration reaction, the evaporation of the solvent is suppressed while water, which is a by-product, is efficiently removed to the outside of the system as described below in detail.

The usual reaction conditions for the method for producing an aromatic nitrile compound according to the present invention may be as follows. The temperature of the reaction solution is 170° C. to 230° C.; the pressure is normal pressure (101.3 (kPa) (760 Torr) to reduced pressure (13.3 (kPa) (100 Torr)); and the time is several hours to about 100 hours. The reaction conditions are not limited to the above.

For example, the temperature of the reaction solution is preferably 180 to 228° C., and more preferably 190 to 210° C. The reaction pressure is preferably 1.33 to 60 (kPA) (10 to 450 Torr), and more preferably 13.3 to 53.3 (kPa) (100 to 400 Torr). The reaction time is preferably 4 to 24 hours, and more preferably 8 to 24 hours.

In the case where a molecular sieve is used as the dehydration agent, there is no specific limitation on the type or the shape of the molecular sieve. For example, a general molecular sieve that has a high water absorption rate such as 3 A, 4 A, 5 A or the like and is spherical or pellet-like is usable. For example, Zeolum produced by Tosoh Corporation is usable. Preferably, the molecular sieve is dried in advance, for example, at 300 to 500° C. for about 1 hour.

(Example of the Dehydration Reaction)

[Chemical formula 2]

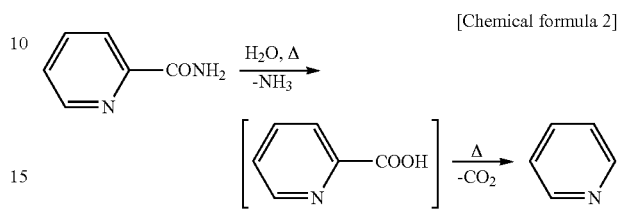

In the dehydration reaction of the aromatic amide compound, it is considered that as shown above, the aromatic amide compound is decomposed to produce an aromatic carboxylic acid, from which pyridine is produced as a by-product. However, a reaction solution obtained after the dehydration reaction performed using the reaction conditions according to the present invention contains an aromatic amide compound in an unreacted state, an aromatic nitrile compound as a reaction product and a solvent, but a by-product such as pyridine shown in the above formula or the like is not generated almost at all.

In the case where a specific solvent compound is used as a solvent in the dehydration reaction described above, an aromatic nitrile compound is selectively produced in a short time as described below in detail. Therefore, any of the four specific solvent compounds is preferably usable for the dehydration reaction.

In the case where, for example, 1,3,5-trimethoxybenzene, among the specific solvent compounds, is used in the above-described dehydration reaction, the reaction phase is entirely liquid, except that the catalyst is solid, for the reason that the melting points of the substances are 110° C. (2-picolinamide), 24° C. (2-cyanopyridine), 19° C. (cyanopyrazine) and 50 to 53° C. (1,3,5-trimethoxybenzene), and the boiling points of the substances are 275° C. (2-picolinamide), 232° C. (2-cyanopyridine), 100° C. (water) and 255° C. (1,3,5-trimethoxybenzene). A reaction distillation device having a decompression device attached thereto is used, the distillation column is heated to have a temperature that is higher than the boiling point of water at the reaction pressure and is lower than the boiling point of 1,3,5-trimethoxybenzene at the reaction pressure, and the reaction solution is heated to have a temperature that is higher than, or equal to, the boiling point of 1,3,5-trimethoxybenzene at the reaction pressure and is lower than the boiling point of 2-picolinamide at the reaction pressure. In this manner, 1,3,5-trimethoxybenzene partially gasified in the reaction system is cooled by a cooling device and returns to the reaction tube, whereas the by-product water is efficiently separated by distillation from the reaction solution and removed to the outside of the system. Therefore, a nitrile regeneration reaction advances at high speed, and thus the time of the dehydration reaction is significantly shortened.

As can be seen, use of, for example, 1,3,5-trimethoxybenzene especially allows the dehydration reaction to be advanced efficiently and allows the aromatic nitrile compound to be recovered easily. Namely, since the boiling points of the substances present in the post-reaction system are different from each other as described above, the components are easily separated from each other by distillation.

It should be noted that even a specific solvent compound having a relatively low boiling point allows an aromatic nitrile compound to be selectively produced in a short time as described above, and thus is considered as being suitable to be used for the dehydration reaction. Therefore, in the dehydration reaction using a specific solvent compound having a relatively low boiling point as a solvent, for example, the reaction conditions such as the temperature and the pressure may be appropriately adjusted, or a mixed solvent containing a compound having a relatively high boiling point together with a specific solvent compound may be used. In this manner, the aromatic amide compound is converted into an aromatic nitrile compound especially efficiently.

<2. Method for Producing a Carbonate Ester Using an Aromatic Nitrile Compound>

As described above, as a result of the dehydration reaction of regenerating an aromatic amide compound into an aromatic nitrile compound, the target compound is obtained selectively at a high yield with no use of a strong reagent and with the generation of a by-product being suppressed. In addition, the reaction speed is significantly improved to significantly shorten the reaction time. Therefore, the speed of regeneration by the dehydration reaction from an aromatic amide compound into an aromatic nitrile compound, and the speed of carbonate ester synthesis from $CO_2$ and an alcohol using the aromatic nitrile compound, are now well balanced; namely, the above-described regeneration and the above-described synthesis may be used together. These reactions may be established as a series of commercial processes. The present inventors applied this knowledge to a carbonate ester production method to conceive the following method for producing a carbonate ester.

(First Reaction Step)

A first reaction step of the method for producing a carbonate ester according to the present invention includes, for example, directly reacting an alcohol and carbon dioxide with each other in the presence of a solid catalyst containing $CeO_2$ (cerium oxide) or the like and an aromatic nitrile compound to generate a carbonate ester (carbonate ester generation reaction).

In this step, an alcohol and carbon dioxide are reacted with each other. As a result, a carbonate ester and also water are generated. The aromatic nitrile compound, which is present in the reaction system, and the generated water are subjected to a hydration reaction to generate an aromatic amide compound. The generated water is removed from the reaction system or decreased in the amount. Water is removed from the reaction system efficiently as described above, so that the generation of the carbonate ester is promoted. For example, the reaction is expressed by the following formula.

[Chemical formula 3]

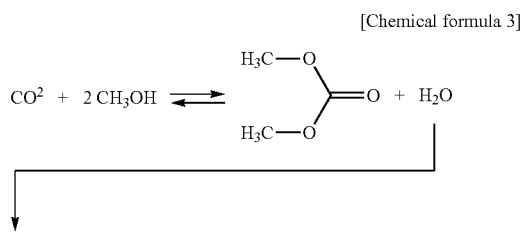

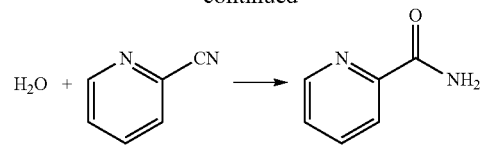

(Alcohol)

As the alcohol, any one, or two or more, selected from primary alcohol, secondary alcohol and tertiary alcohol are usable. Examples of preferable alcohols include methanol, ethanol, 1-propanol, isopropanol, 1-butanol, 1-pentanol, 1-hexanol, 1-heptanol, 1-octanol, 1-nonanol, allylalcohol, 2-methyl-1-propanol, cyclohexanemethanol, benzylalcohol, ethyleneglycol, 1,2-propanediol, and 1,3-propanediol. These alcohols increase the yield of the target product and also increase the reaction speed. The carbonate esters generated by use of the above-listed alcohols are respectively dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonane carbonate, diallyl carbonate, di-2-methyl-propyl carbonate, dicyclohexanemethyl carbonate, dibenzyl carbonate, ethylene carbonate, 1,2-propylene carbonate, and 1,3-propylene carbonate.

In the case where the obtained carbonate ester is used as a material of diallyl carbonate, it is preferable to use an alcohol having a carbon number of 1 to 6, and it is more preferable to use an alcohol having a carbon number of 2 to 4.

It is preferable to use a monohydric alcohol or a dihydric alcohol.

(Catalyst Usable for Producing a Carbonate Ester)

In the first reaction step of the method for producing a carbonate ester, it is preferable to use one or both of $CeO_2$ and $ZrO_2$ as a solid catalyst. For example, it is preferable to use only $CeO_2$, only $ZrO_2$, a mixture of $CeO_2$ and $ZrO_2$, a solid solution of $CeO_2$ and $ZrO_2$, or a composite oxide of $CeO_2$ and $ZrO_2$. It is especially preferable to use only $CeO_2$. The mixing ratio of $CeO_2$ and $ZrO_2$ in the solid solution or the composite oxide is basically 50:50, but may be changed appropriately.

The catalyst used in the first reaction step may be in the form of powder or a molded body. In the case of being a molded body, the catalyst may be spherical, pellet-like, cylindrical, ring-shaped, wheel-shaped, granular or the like.

(Carbon Dioxide)

In the present invention, carbon dioxide prepared as industrial gas, or carbon dioxide separated and recovered from exhaust gas of plants producing various products, steel manufacturing plants, power plants or the like, is usable.

(Solvent in the Carbonate Ester Generation Reaction)

For the carbonate ester generation reaction, it is preferable to use a solvent having a boiling point higher than that of the amide compound to be produced. More preferably, the solvent in the carbonate ester generation reaction contains at least one of dialkylbenzene, alkylnaphthalene, and diphenylbenzene. Specific examples of preferable solvents include barrel process oil B28AN and barrel process oil B30 (produced by Matsumura Oil Co., Ltd.), each of which a contains component such as dialkylbenzene, alkylnaphthalene, diphenylbenzene or the like.

(Separation by Distillation)

After the reaction, the obtained substance may be distilled to be separated into a carbonate ester as a main product, an aromatic amide compound as a by-product, an unreacted aromatic nitrile compound, and a solid catalyst such as $CeO_2$ or the like. Thus, the products are recovered.

(Second Reaction Step)

In a second reaction step according to the present invention, the aromatic amide compound generated as a by-product in the first reaction step is separated from, preferably, the system obtained after the carbonate ester generation reaction, and then an aromatic nitrile compound is produced by a dehydration reaction. The second reaction step corresponds to the above-described method for producing the aromatic nitrile compound, and thus will not be described in detail.

(Reuse of the Aromatic Nitrile Compound)

The aromatic nitrile compound regenerated by the second reaction step is reusable for the first reaction step (hydration reaction).

According to the present invention, as described above, a solvent containing a specific solvent compound is used in the dehydration reaction of an aromatic amide compound, so that an aromatic nitrile compound is efficiently regenerated from the aromatic amide compound while generation of a by-product is suppressed. In addition, for example, the temperature of the reaction solution is adjusted, so that the step of solid-liquid separation of the catalyst is made unnecessary, and also the aromatic nitrile compound is easily recovered. In the carbonate ester generation reaction, a catalyst having a boiling point higher than that of aromatic carboamide is used, so that the step of solid-liquid separation of the catalyst is made unnecessary. As can be seen, according to the present invention, an aromatic nitrile compound is selectively regenerated from an aromatic amide compound, and a series of reactions are allowed to be advanced while the components are separated from each other only by distillation without a step of solid-liquid separation of the catalyst. Thus, an efficient process as described below in detail is realized.

<3. Device for Producing a Carbonate Ester>

Figure 2:
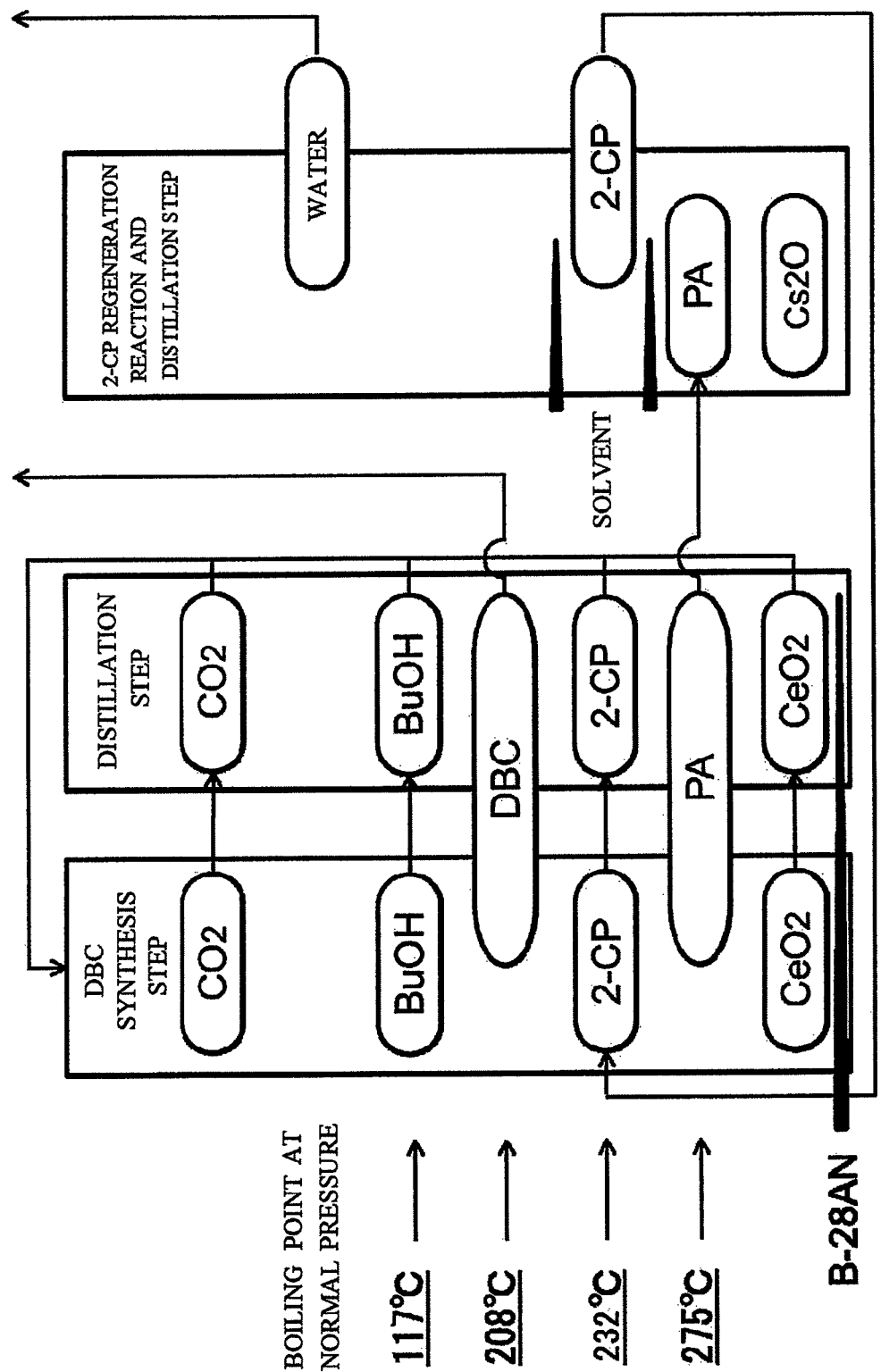
FIG. 2 is a chart showing the state of each of substances at each of steps in the production performed by use of the production device shown in FIG. 1.

Now, a production device usable in the present invention will be described in detail by way of a specific example. FIG. 1 shows an example of preferable production device. FIG. 2 schematically shows the state of each of the substances in each of the steps performed by the production device.

(First Reaction Step)

In the first reaction step, a carbonate ester reactor 1 (first reaction portion) is filled with one or both of $CeO_2$ and $ZrO_2$ as a solid catalyst (solid phase), alcohol (1-butanol (BuOH); liquid phase), 2-cyanopyridine (2-CP; liquid), barrel process oil (B28AN; liquid phase) as a solvent, and carbon dioxide ($CO_2$; gas phase) supplied via a pressure raising blower (not shown). The solid catalyst ($CeO_2$; solid phase) may be newly supplied before the reaction or recovered from a catalyst separation column 2. New 2-cyanopyridine is used at the start of the reaction. Alternatively, unreacted 2-cyanopyridine 19 (gas phase) separated and purified in a dehydration agent separation column 3 and an amide separation column 4, and 2-cyanopyridine 22 (liquid phase; 2-cyanopyridine 26 via a solvent recovery column 24) regenerated from 2-picolinamide purified in a water separation column 7, are reusable.

In a direct synthesis device for a carbonate ester usable in the present invention, one or both of $CeO_2$ and $ZrO_2$ are used as a solid catalyst. The synthesis device may be a flow reactor such as a batch reactor, a semi-batch reactor, a continuous tank reactor, a tube reactor or the like.

(Temperature of the Reaction Solution)

The temperature of the reaction solution in the carbonate ester reactor 1 is preferably 50 to 300° C. In the case where the temperature of the reaction solution is lower than 50° C., the reaction speed is low, and the carbonate ester synthesis reaction or the hydration reaction with 2-cyanopyridine does not advance almost at all. In this case, the productivity of the carbonate ester tends to be low. In the case where the temperature of the reaction solution is higher than 300° C., the reaction speed of each reaction is high, but the carbonate ester is easily decomposed or denatured and 2-picolinamide is easily reacted with an alcohol. Therefore, the yield of the carbonate ester tends to be low. The temperature of the reaction solution is more preferably 100 to 150° C. An ideal temperature of the reaction solution is considered to vary in accordance with the type or the amount of the solid catalyst, or the amount or the ratio of the materials (alcohol and 2-cyanopyridine). Thus, it is desirable to set the optimal temperature appropriately. Since the preferable temperature of the reaction solution is 100 to 150° C., it is desirable to pre-heat the materials (alcohol and 2-cyanopyridine) with steam or the like on a stage before the carbonate ester reactor.

(Reaction Pressure)

The reaction pressure in the carbonate ester reactor 1 is preferably 0.1 to 20 MPa (absolute pressure). In the case where the reaction pressure is lower than 0.1 MPa (absolute pressure), a decompression device is required, which makes the facilities complicated and costly. In addition, a motive power energy to reduce the pressure is necessary, which decreases the energy efficiency. In the case where the reaction pressure is higher than 20 MPa, the hydration reaction with 2-cyanopyridine does not easily advance, which decreases the yield of the carbonate ester. In addition, a motive power energy to raise the pressure is necessary, which decreases the energy efficiency. From the point of view of increasing the yield of the carbonate ester, the reaction pressure is more preferably 0.5 to 15 MPa (absolute pressure), and still more preferably 1.0 to 10 MPa (absolute pressure).

(Amount of 2-Cyanopyridine)

2-cyanopyridine to be used for the hydration reaction is desirably introduced into the reactor before the reaction in a molar amount that is 0.2 times or greater and 5 times or less of the theoretical molar amount of water generated as a by-product by the reaction of the alcohol and $CO_2$ as the materials. The molar amount of 2-cyanopyridine is more desirably, 0.5 times or greater and 3 times or less, and especially desirably 0.8 times or greater and 1.5 times or less, of the theoretical molar amount of water generated as a by-product by the reaction of the alcohol and $CO_2$ as the materials. In the case where the molar amount of 2-cyanopyridine is too small, the amount of 2-cyanopyridine contributing to the hydration reaction is small, which may undesirably decrease the yield of the carbonate ester. By contrast, in the case where the molar amount of 2-cyanopyridine is too large with respect to the alcohol as a material, the by-reaction of 2-cyanopyridine is undesirably increased. The ideal amounts of the alcohol and 2-cyanopyridine with respect to the solid catalyst are considered to vary in accordance with the type or the amount of the solid catalyst, the type of the alcohol, or the ratio of the alcohol and 2-cyanopyridine. Thus, it is desirable to set the optimal conditions appropriately.

(Separation of the Reaction Products)

Preferably, the separation of the reaction products is entirely performed by distillation. After the reaction in the carbonate ester reactor 1, a reaction solution 10 is transported to the catalyst separation column 2. From the bottom of the catalyst separation column 2, the catalyst and the solvent (in this example, barrel process oil (B28AN) (liquid phase; 11)) are recovered. From the top of the catalyst separation column 2, $CO_2$ (12) and a mixture (13) of BuOH, dibutyl carbonate (DBC), 2-cyanopyridine and 2-picolinamide are recovered. The catalyst, the solvent and $CO_2$ that are recovered are recycled to the carbonate ester reactor 1.

The mixture (13) recovered from the catalyst separation column 2 is transported to the dehydration agent separation column 3. From the bottom of the dehydration agent separation column 3, a mixture (14) of 2-cyanopyridine and 2-picolinamide is recovered. From the top of the dehydration agent separation column 3, BuOH and DBC (15) are recovered.

The mixture (14) recovered from the bottom of the dehydration agent separation column 3 is transported to the amide separation column 4. From the bottom of the amide separation column, 2-picolinamide (18) is recovered. From the top of the amide separation column, the 2-cyanopyridine (19) is recovered. The recovered 2-cyanopyridine is recycled to the carbonate ester reactor 1. The 2-picolinamide (18) recovered from the bottom of the amide separation column 4 is transported to a nitrile regeneration reactor 6.

The BuOH and the DBC (15) recovered from the top of the dehydration agent separation column 3 are transported to a carbonate ester recovery column 5. From the bottom of the carbonate ester recovery column, DBC (16) is recovered. From the top of the carbonate ester recovery column, BuOH (17) is recovered. The recovered BuOH is recycled to the carbonate ester reactor 1.

The 2-picolinamide (2-PA; 18) recovered from the amide separation column 4 is transferred to the nitrile regeneration reactor 6 (second reaction portion) to be regenerated into 2-cyanopyridine.

(Second Reaction Step)

In the second reaction step, 2-cyanopyridine (2-CP) is generated by a dehydration reaction of 2-picolinamide in the nitrile regeneration reactor 6. The production device used in the present invention (nitrile regeneration reactor 6) performs the dehydration reaction of 2-picolinamide in the presence of a catalyst containing a carried basic metal oxide and a solvent containing a specific solvent compound to generate 2-cyanopyridine. There is no specific limitation on the form of the reaction. A flow reactor such as a batch reactor, a semi-batch reactor, a continuous tank reactor, a tube reactor or the like is usable. For the catalyst, a fixed bed, a slurry bed or the like is usable. The temperature of the nitrile regeneration reactor 6 is variable in accordance with the form of the reaction. A reaction distillation device having a decompression device attached thereto is used. Preferably, the distillation column is heated to have a temperature that is higher than the boiling point of water at the reaction pressure and is lower than the boiling point of the solvent at the reaction pressure. As described above, the temperature of the reaction solution is adjusted to be higher than, or equal to, the boiling point of the solvent at the pressure reaction and lower than the boiling point of 2-picolinamide at the reaction pressure. With such an arrangement, the solvent partially gasified in the reaction system is cooled by a cooling device and returns to the reaction tube. The by-product water is efficiently separated by distillation from the reaction solution and removed to the outside of the system. Therefore, the nitrile regeneration reaction advances at high speed.

Among 1,2,3,4-tetrahydronaphthalene, 1,2-dimethoxybenzene, 1,3-dimethoxybenzene and 1,3,5-trimethoxybenzene as the specific solvent compounds, any of the three compounds having a relatively low boiling point other than 1,3,5-trimethoxybenzene may be used as a main component of a solvent. In such a case, the solvent recovery column 24 may be provided, so that the solvent is recovered efficiently. Namely, the solvent recovery column 24 shown in FIG. 1 may be provided, so that a first recovered solvent (21) recovered from the water separation column 7 and also a second recovered solvent (25) separated from the 2-cyanopyridine (22) in the solvent recovery column 24 are reusable.

The 2-cyanopyridine (22) may be recovered from the water separation column 7 during the reaction or separated by distillation and recovered after the reaction. The recovered 2-cyanopyridine 22 is transported to the carbonate ester reactor 1 and reused for the production of the carbonate ester.

As described above, according to the present invention, a reaction product and a compound to be reused are separated from each other merely by distillation, with no need of solid-liquid separation. Therefore, according to the present invention, a carbonate ester is produced efficiently with a simpler production device and a smaller number of production steps.

EXAMPLES

Hereinafter, the present invention will be described in more detail by way of examples. The present invention is not limited to any of the following examples. First, examples and comparative examples of method for producing cyanopyridine will be described.

Examples 1 Through 6

In examples 1 through 6, only a specific solvent compound was used as the solvent to perform the dehydration reaction.

Example 1

$SiO_2$ (CARiACT, G-6, surface area: 535 m$^2$/g; produced by Fuji Silysia Chemical Ltd.) for a carrier was sized to 100 mesh or less, and pre-baked at 700° C. for about 1 hour. Then, in order to cause Cs to be carried as an alkaline metal, an aqueous solution was prepared using $Cs_2CO_3$ (produced by Wako Pure Chemical Industries, Ltd.) such that the final amount of Cs metal to be carried would be 0.5 mmol/g, and $SiO_2$ was impregnated with the aqueous solution. Then, the resultant substance was dried at 110° C. for about 6 hours and was baked at 500° C. for about 3 hours. As a result, a $Cs_2O/SiO_2$ catalyst was obtained. An $Na_2O/SiO_2$ catalyst used in some of comparative examples described below was produced by substantially the same method as the $Cs_2O/SiO_2$ catalyst.

Next, a 3-necked round-bottom flask was used as a reactor. A magnetic stirrer, the $Cs_2O/SiO_2$ catalyst (1.0 g (Cs: 0.5 mmol)), 2-picolinamide (2-PA; 6.1 g (50 mmol); produced by Tokyo Chemical Industry Co., Ltd.), and 1,3-dimethoxybenzene (51.8 g (375 mmol); produced by Tokyo Chemical Industry Co., Ltd.) were introduced into the reactor.

A thermometer and an air-cooling tube containing 10 g of molecular sieve 4A were attached to the reactor. A Liebig condenser was attached to a top end of the air-cooling tube. The resultant device was to be used as a reaction device.

Then, the reaction was performed in a state where the reaction solution was heated at the normal pressure and kept in a boiled state while by-product water was adsorbed to the molecular sieve without being returned to the reactor.

The start of the reaction was set to the timing when the reaction solution started to be boiled, and the reaction was continued for 24 hours.

After the reaction, the temperature was cooled to room temperature. The reaction solution was sampled and diluted two-fold with ethanol, and 1-hexanol was added thereto as an internal standard substance. The resultant substance was subjected to a qualitative analysis with GC-MS (gas chromatograph-mass spectrometer) and to a quantitative analysis with FID-GC. As a result, 2-cyanopyridine was found to be generated as shown in Table 1. The yield of 2-cyanopyridine was 69.1 mol %, and the generation ratio of pyridine as a by-product was suppressed to 0.88 mol % (see Table 1).

Examples 2 and 3

In examples 2 and 3, the reaction was performed in substantially the same manner as in example 1 with different specific solvent compounds. The results are shown in Table 1.

Example 4

A $Cs_2O/SiO_2$ catalyst was produced in the same step as in example 1. Next, a 3-necked round-bottom flask was used as a reactor. A magnetic stirrer, the $Cs_2O/SiO_2$ catalyst (1.0 g (Cs: 0.5 mmol)), 2-picolinamide (2-PA; 6.1 g (50 mmol); produced by Tokyo Chemical Industry Co., Ltd.), and 1,3,5-trimethoxybenzene (176.6 g (1.05 mol; produced by Tokyo Chemical Industry Co., Ltd.) were introduced into the reactor.

Then, a thermometer was attached to the reactor. A distilling head having a thermometer attached thereto was attached to a top end of a first air-cooling tube. A second air-cooling tube, a receiver, and a vacuum pump were connected to the distilling head. The resultant device was to be used as a reaction distillation device. A ribbon heater was wound around the first air-cooling tube, so that the temperature of the first air-cooling tube would be adjustable. A cooling trap was cooled with liquid nitrogen, so that gasified pyridine would be recovered.

Then, the pressure in the reaction distillation device was reduced by the vacuum pump to 52.3 kPa (392 Torr). The first air-cooling tube was heated to 87° C., which was higher than the boiling point of water at the reaction pressure and lower than the boiling point of 1,3,5-trimethoxybenzene at the reaction pressure. The reaction solution was maintained in a boiled state at 229° C., which was higher than, or equal to, the boiling point of 1,3,5-trimethoxybenzene at the reaction pressure and lower than the boiling point of 2-picolinamide at the reaction pressure. The temperatures were adjusted in this manner, so that the reaction was performed in a state where 1,3,5-trimethoxybenzene partially gasified in the reaction system was cooled in the first air-cooling tube and returned to the reactor while the by-product water was separated by distillation and removed to the outside of the system without being returned to the reactor.

The start of the reaction was set to the timing when the reaction solution started to be boiled, and the reaction was continued for 4 hours.

After the reaction, the reaction solution was cooled to room temperature. The reaction solution was sampled and diluted two-fold with ethanol, and 1-hexanol was added thereto as an internal standard substance. The resultant substance was subjected to a qualitative analysis with GC-MS (gas chromatograph-mass spectrometer) and to a quantitative analysis with FID-GC. As a result, 2-cyanopyridine was found to be generated as shown in Table 1. The yield of 2-cyanopyridine was 53.1 mol %, and the generation ratio of pyridine as a by-product was suppressed to 1.67 mol % (see Table 1).

Examples 5 and 6

In examples 5 and 6, the reaction was performed in substantially the same manner as in example 1 with a mixture of specific solvent compounds. The results are shown in Table 2.

In examples 1 through 6, the aromatic nitrile compound (2-cyanopyridine) was generated at a high yield while the generation of pyridine as a main by-product was suppressed as described below in detail.

Examples 7 Through 12

In each of examples 7 through 9 and 11, the dehydration reaction was performed in substantially the same manner as in embodiment 4 using a solvent containing a specific solvent compound and also diphenylether as another component. As a result of these examples, it has been confirmed that even in the case where a mixed solvent having a total amount of the four specific solvent compounds of 20 to 60% by weight is used, a high nitrile selectivity (mol %) (amount of aromatic nitrile compound (mol)/(amount of pre-reaction aromatic amide compound (mol)−amount of post-reaction aromatic amide compound (mol))×100) is realized in a dehydration reaction having a relatively short reaction time of 6 hours or 12 hours (see Table 3). Namely, as shown in examples 7 through 9 and 11 and the graph in FIG. 3, use of a mixed solvent containing 20% by weight or greater of 1,3-dimethoxybenzene, which was one of the specific solvent compounds, realized a high nitrile selectivity of 80 mol % or higher.

In examples 7 through 9 and 11 with a short reaction time, the yield of the aromatic nitrile compound (nitrile yield) is considered as not being as high as in examples 1 through 6. However, in examples 10 and 12, in which only 1,3-dimethoxybenzene as a specific solvent compound was used as the solvent, and the dehydration reaction was performed with a reaction time of 6 hours or 12 hours, like in examples 7 through 9 using the mixed solvents; the yield of the aromatic nitrile compound was generally equal to the yield in examples 7 through 9 (see Table 3). In example 1, the dehydration reaction was performed for a longer time of 24 hours using only 1,3-dimethoxybenzene as the solvent, and a high nitrile yield of about 70% was realized. In consideration of these results, it is considered that even in a dehydration reaction using a mixed solvent in examples 7 and thereafter, a high nitrile yield would be realized in accordance with the reaction time.

Comparative Examples 1 Through 17

In the meantime, in comparative examples 1 through 17, a solvent containing none of the four specific solvent compounds was used. In comparative examples 10, 14 and 16, the dehydration reaction was performed in substantially the same manner as in example 4. In the other comparative examples, the dehydration reaction was performed in substantially the same manner as in example 1. As a result, 2-cyanopyridine was produced from 2-picolinamide (see Table 4).

In comparative example 1 with a significantly longer reaction time of 400 hours, an aromatic nitrile compound was generated at a high yield, and the generation of pyridine as a by-product was suppressed. However, the dehydration reaction requiring such a long reaction time is not suitable to practical use. In comparative examples 2 and thereafter with a reaction time of 24 hours (only in comparative example 10, the reaction time was 12 hours), the nitrile yield was significantly lower, and the generation amount of pyridine with respect to the generation amount of the nitrile compound (2-cyanopyridine) was larger, than in examples 1 through 6 having a reaction amount of 24 hours or significantly shorter than 24 hours.

The results in examples 1 through 12 and comparative examples 1 through 17 are shown in Tables 1 through 4 below.

TABLE 1

| Example | Substrate | Substrate amount mmol | Catalyst type | Catalyst amount mol % | Solvent | Solvent boiling point ° C. | Solvent amount Molar ratio | Reaction solution temperature ° C. | Reaction solution state |
|---|---|---|---|---|---|---|---|---|---|
| Example 1 | 2-PA | 15 | $Cs_2O/SiO_2$ | 1.0 | 1,3-Dimethoxybenzene | 217 | 25 | 215 | Boiled |
| Example 2 | 2-PA | 15 | $Cs_2O/SiO_2$ | 1.0 | 1,2,3,4-tetrahydronaphthalene | 207 | 25 | 210 | Boiled |
| Example 3 | 2-PA | 15 | $Cs_2O/SiO_2$ | 1.0 | 1,2-Dimethoxybenzene | 207 | 25 | 210 | Boiled |
| Example 4 | 2-PA | 50 | $Cs_2O/SiO_2$ | 1.0 | 1,3,5-Trimethoxybenzene | 255 | 21 | 229 | Boiled |

| Example | Reaction pressure kPa | Reaction pressure Torr | 1st air-cooling tube temperature ° C. | Reaction time h | Dehydration method | Nitrile yield mol % | Pyridine generation ratio mol % | 2-CP selectivity mol % | Nitrile/pyridine mol %/mol % |
|---|---|---|---|---|---|---|---|---|---|
| Example 1 | 101.3 | 760 | — | 24 | Molecular sieve | 69.1 | 0.88 | — | 79 |
| Example 2 | 101.3 | 760 | — | 24 | Molecular sieve | 56.5 | 0.65 | — | 87 |
| Example 3 | 101.3 | 760 | — | 24 | Molecular sieve | 54.6 | 0.46 | — | 119 |
| Example 4 | 52.3 | 392 | 87 | 4 | Distillation and removal at reduced pressure | 53.1 | 1.67 | — | 32 |

TABLE 2

| Example | Substrate | Substrate amount mmol | Catalyst type | Catalyst amount mol % | Solvent | Solvent boiling point ° C. | Solvent amount g | Solvent amount Molar ratio |
|---|---|---|---|---|---|---|---|---|
| Example 5 | 2-PA | 50 | $Cs_2O/SiO_2$ | 1.0 | 1,2,3,4-tetrahydronaphthalene/ 1,3-Dimethoxybenzene = 50/50(wt %) | 211 | 183 | 27 |
| Example 6 | 2-PA | 50 | $Cs_2O/SiO_2$ | 1.0 | 1,3-Dimethoxybenzene/ 1,3,5-Trimethoxybenzene = 50/50(wt %) | 230 | 183 | 24 |

| Example | Reaction solution temperature ° C. | Reaction solution state | Reaction pressure kPa | Reaction pressure Torr | Reaction time h | Dehydration method | Nitrile yield mol % | Pyridine generation ratio mol % | Nitrile/pyridine mol %/mol % |
|---|---|---|---|---|---|---|---|---|---|
| Example 5 | 214 | Boiled | 101.3 | 760 | 24 | Molecular sieve | 62.8 | 0.77 | 82 |
| Example 6 | 233 | Boiled | 101.3 | 760 | 4 | Molecular sieve | 65.1 | 1.10 | 59 |

TABLE 3

| Example | Substrate | Substrate amount mmol | Catalyst type | Catalyst amount mol % | Solvent | Solvent boiling point °C | Solvent amount g | Solvent amount Molar ratio | Reaction solution temperature °C | Reaction solution state |
|---|---|---|---|---|---|---|---|---|---|---|
| Example 7 | 2-PA | 50 | $Cs_2O/SiO_2$ | 1.0 | 1,3-Dimethoxybenzene/Diphenyleter = 60/40 (wt %) | 227 | 183 | 24 | 195 | Boiled |
| Example 8 | 2-PA | 50 | $Cs_2O/SiO_2$ | 1.0 | 1,3-Dimethoxybenzene/Diphenyleter = 40/60 (wt %) | 234 | 183 | 24 | 195 | Boiled |
| Example 9 | 2-PA | 50 | $Cs_2O/SiO_2$ | 1.0 | 1,3-Dimethoxybenzene/Diphenyleter = 20/80 (wt %) | 244 | 183 | 23 | 200 | Boiled |
| Example 10 | 2-PA | 50 | $Cs_2O/SiO_2$ | 1.0 | 1,3-Dimethoxybenzene | 217 | 182 | 26 | 194 | Boiled |
| Example 11 | 2-PA | 50 | $Cs_2O/SiO_2$ | 1.0 | 1,3-Dimethoxybenzene/Diphenyleter = 60/40 (wt %) | 227 | 183 | 25 | 195 | Boiled |
| Example 12 | 2-PA | 50 | $Cs_2O/SiO_2$ | 1.0 | 1,3-Dimethoxybenzene | 217 | 182 | 26 | 194 | Boiled |

| Example | Reaction pressure kPa | Reaction pressure Torr | 1st air-cooling tube temperature °C | Reaction time h | Dehydration method | Nitrile yield mol % | Pyridine generation ratio mol % | 2-CP selectivity mol % | Nitrile/pyridine mol %/mol % |
|---|---|---|---|---|---|---|---|---|---|
| Example 7 | 42.0 | 315 | 50 | 6 | Distillation and removal at reduced pressure | 13.4 | Below the detection limit | 100.0 | — |
| Example 8 | 34.3 | 257 | 50 | 6 | Distillation and removal at reduced pressure | 14.4 | Below the detection limit | 95.8 | — |
| Example 9 | 29.6 | 222 | 50 | 6 | Distillation and removal at reduced pressure | 8.2 | 0.050 | 80.4 | 164 |
| Example 10 | 53.6 | 402 | 50 | 6 | Distillation and removal at reduced pressure | 14.4 | 0.079 | 99.9 | 183 |
| Example 11 | 42.0 | 315 | 50 | 12 | Distillation and removal at reduced pressure | 22.8 | 0.29 | 96.5 | 78 |
| Example 12 | 53.6 | 402 | 50 | 12 | Distillation and removal at reduced pressure | 25.6 | 0.25 | 96.8 | 104 |

TABLE 4

| Comparative example | Substrate | Substrate amount mmol | Catalyst type | Catalyst amount mol % | Solvent | Solvent boiling point °C | Solvent amount Molar ratio | Reaction solution temperature °C | Reaction solution state |
|---|---|---|---|---|---|---|---|---|---|
| Comparative example 1 | 2-PA | 5 | $Na_2O/SiO_2$ | 1.0 | Mesitylene | 165 | 25 | 165 | Boiled |
| Comparative example 2 | 2-PA | 5 | $Na_2O/SiO_2$ | 1.0 | Mesitylene | 165 | 25 | 165 | Boiled |
| Comparative example 3 | Pyrazinamide | 15 | $Cs_2O/SiO_2$ | 1.0 | Mesitylene | 165 | 25 | 165 | Boiled |
| Comparative example 4 | 2-PA | 15 | $Na_2O/SiO_2$ | 1.0 | 3,4-Dimethoxytoluene | 218 | 25 | 223 | Boiled |
| Comparative example 5 | 2-PA | 15 | $Cs_2O/SiO_2$ | 1.0 | 1-tert-Butyl-3,5-Dimethylbenzene | 202 | 25 | 204 | Boiled |
| Comparative example 6 | 2-PA | 15 | $Cs_2O/SiO_2$ | 1.0 | Cyclohexylbenzene | 236 | 25 | 202 | Not boiled |
| Comparative example 7 | 2-PA | 15 | $Cs_2O/SiO_2$ | 1.0 | 3,5-Dimethylanisole | 193 | 25 | 195 | Boiled |
| Comparative example 8 | 2-PA | 15 | $Na_2O/SiO_2$ | 1.0 | 3-Methylanisole | 177 | 25 | 180 | Boiled |
| Comparative example 9 | 2-PA | 15 | $Cs_2O/SiO_2$ | 1.0 | 4-tert-Butylanisole | 222 | 25 | 202 | Not boiled |
| Comparative example 10 | 2-PA | 50 | $Cs_2O/SiO_2$ | 1.0 | Dihenyl Sulfide | 296 | 25 | 182 | Boiled |
| Comparative example 11 | 2-PA | 15 | $Cs_2O/SiO_2$ | 1.0 | Dihenyl Sulfide | 296 | 25 | 202 | Not boiled |
| Comparative example 12 | 2-PA | 7.5 | $Na_2O/SiO_2$ | 1.0 | Amylbenzene | 205 | 25 | 207 | Boiled |

TABLE 4-continued

| | | | | | | | | | |
|---|---|---|---|---|---|---|---|---|---|
| Comparative example 13 | 2-PA | 15 | $Cs_2O/SiO_2$ | 1.0 | 1-Methylnaphthalene | 241 | 25 | 203 | Not boiled |
| Comparative example 14 | 2-PA | 15 | $Cs_2O/SiO_2$ | 1.0 | 1-Methoxynaphthalene | 271 | 25 | 202 | Not boiled |
| Comparative example 15 | 2-PA | 15 | $Cs_2O/SiO_2$ | 1.0 | Diamyl Ether | 186 | 25 | 189 | Boiled |
| Comparative example 16 | 2-PA | 15 | $Cs_2O/SiO_2$ | 1.0 | Dibenzyl Ether | 298 | 25 | 201 | Not boiled |
| Comparative example 17 | 2-PA | 15 | $Cs_2O/SiO_2$ | 1.0 | Diethylene Glycol Diethyl Ether | 188 | 25 | 191 | Boiled |

| Comparative example | Reaction pressure kPa | Reaction pressure Torr | 1st air-cooling tube temperature °C. | Reaction time h | Dehydration method | Nitrile yield mol % | Pyridine generation ratio (*1) mol % | 2-CP selectivity mol % | Nitrile/ pyridine (*2) mol %/mol % |
|---|---|---|---|---|---|---|---|---|---|
| Comparative example 1 | 101.3 | 760 | — | 400 | Molecular sieve | 79.2 | 0.34 | — | 232 |
| Comparative example 2 | 101.3 | 760 | — | 24 | Molecular sieve | 9.9 | Below the detection limit | — | — |
| Comparative example 3 | 101.3 | 760 | — | 24 | Molecular sieve | 2.70 | Below the detection limit | — | — |
| Comparative example 4 | 101.3 | 760 | — | 24 | Molecular sieve | 13.3 | 1.88 | — | 7 |
| Comparative example 5 | 101.3 | 760 | — | 24 | Molecular sieve | 20.0 | 3.60 | — | 6 |
| Comparative example 6 | 101.3 | 760 | — | 24 | Molecular sieve | 4.82 | 1.52 | — | 3 |
| Comparative example 7 | 101.3 | 760 | — | 24 | Molecular sieve | 0.49 | 0.12 | — | 4 |
| Comparative example 8 | 101.3 | 760 | — | 24 | Molecular sieve | 2.54 | Below the detection limit | — | |
| Comparative example 9 | 101.3 | 760 | — | 24 | Molecular sieve | 16.0 | 0.49 | — | 32 |
| Comparative example 10 | 6.13 | 46 | 45 | 12 | Distillation and removal at reduced pressure | 18.3 | 0.35 | — | 53 |
| Comparative example 11 | 101.3 | 760 | — | 24 | Molecular sieve | 17.4 | 1.28 | — | 14 |
| Comparative example 12 | 101.3 | 760 | — | 24 | Molecular sieve | Non-adoptable because the reaction solution is blackened by the by-product | | — | — |
| Comparative example 13 | 101.3 | 760 | — | 24 | Molecular sieve | Non-adoptable because the reaction solution is blackened by the by-product | | — | — |
| Comparative example 14 | 101.3 | 760 | — | 24 | Molecular sieve | Non-adoptable because the reaction solution is blackened by the by-product | | — | — |
| Comparative example 15 | 101.3 | 760 | — | 24 | Molecular sieve | Non-adoptable because the reaction solution is blackened by the by-product | | — | — |
| Comparative example 16 | 101.3 | 760 | — | 24 | Molecular sieve | Non-adoptable because the reaction solution is blackened by the by-product | | — | — |
| Comparative example 17 | 101.3 | 760 | — | 24 | Molecular sieve | Non-adoptable because the reaction solution is blackened by the by-product | | — | — |

(*1) In comparative example 3, pyrazine generation ratio (mol %)
(*2) In comparative example 3, nitrile/pyrazine (mol %/mol %)

As described above, the dehydration reaction in examples 1 through 12 using a specific solvent compound as a solvent resulted in generating the aromatic nitrile compound as a target compound at a high yield while suppressing the generation of a by-product such as pyridine or the like. Especially in examples 1 through 5 and 7 through 12, in which the temperature of the reaction solution was adjusted to the range of 170° C. to 230° C., a high yield of the nitrile compound and the reduction of the generation of the by-product were both confirmed be realized.

Figure 4:
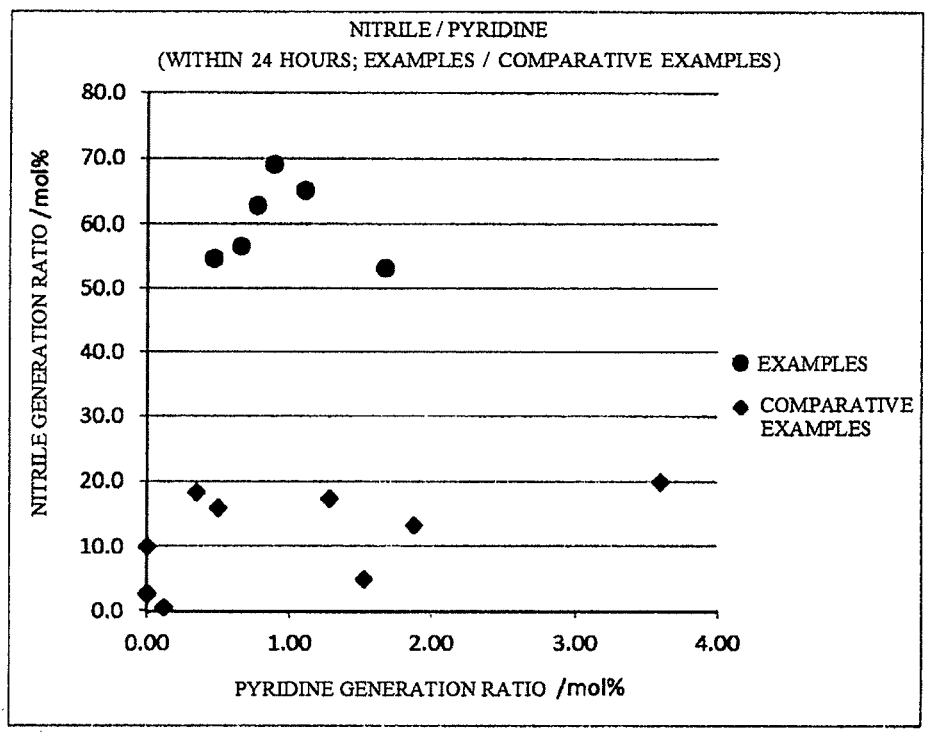
FIG. 4 is a graph showing the ratio of the yields (generation ratios) of nitrile and pyridine in an example and a comparative example.

By contrast, the comparative examples, in which a solvent containing none of the specific solvent compounds was used, resulted in a low yield of the aromatic nitrile compound (see FIG. 4, which shows the results of the examples and the comparative examples exhibiting a relatively high yield). In some of the comparative examples, the generation of pyridine was suppressed. However, even in these comparative examples, the nitride yield was low. In comparative example 1, the nitrile yield was high, but the required reaction time was too long. Thus, comparative example 1 was inferior to the examples.

For evaluation of the catalysts, control tests were performed among which only the type of the catalyst was different. The catalysts used were the catalysts usable for the dehydration reaction. In the control tests, the type of the solvent was different from that in example 1 and the like.

The tests were performed under the reaction conditions suitable to the boiling point of the solvent. The results are shown in Table 5.

It has been confirmed that in the case where, as described above, 1,3-dimethoxybenzene is used and the temperature of the reaction solution is adjusted by pressure control, the reaction speed is significantly improved to shorten the reaction time, the target compound is obtained selectively at a high yield, and the aromatic nitrile compound is recovered easily.

TABLE 5

| Reference example | Substrate | Substrate amount mmol | Catalyst type | Catalyst amount mol % | Solvent | Solvent boiling point °C. | Solvent amount Molar ratio | Reaction solution temperature °C. |
|---|---|---|---|---|---|---|---|---|
| Reference example 1 | 2-PA | 5 | $Li_2O/SiO_2$ | 1.0 | Mesitylene | 165 | 25 | 165 |
| Reference example 2 | 2-PA | 5 | $Na_2O/SiO_2$ | 1.0 | Mesitylene | 165 | 25 | 165 |
| Reference example 3 | 2-PA | 5 | $K_2O/SiO_2$ | 1.0 | Mesitylene | 165 | 25 | 165 |
| Reference example 4 | 2-PA | 5 | $Rb_2O/SiO_2$ | 1.0 | Mesitylene | 165 | 25 | 165 |
| Reference example 5 | 2-PA | 5 | $Cs_2O/SiO_2$ | 1.0 | Mesitylene | 165 | 25 | 165 |
| Reference example 6 | 2-PA | 5 | $CaO/SiO_2$ | 1.0 | Mesitylene | 165 | 25 | 165 |
| Reference example 7 | 2-PA | 5 | $CeO_2$ | 1.0 | Mesitylene | 165 | 25 | 165 |
| Reference example 8 | 2-PA | 5 | $MoO_3/SiO_2$ | 1.0 | Mesitylene | 165 | 25 | 165 |

| Reference example | Reaction solution state | Reaction pressure kPa | Reaction pressure Torr | Reaction time h | Dehydration method | Nitrile yield mol % | Pyridine generation ratio mol % |
|---|---|---|---|---|---|---|---|
| Reference example 1 | Boiled | 101.3 | 760 | 24 | Molecular sieve | 2.91 | Below the detection limit |
| Reference example 2 | Boiled | 101.3 | 760 | 24 | Molecular sieve | 9.9 | Below the detection limit |
| Reference example 3 | Boiled | 101.3 | 760 | 24 | Molecular sieve | 16.0 | Below the detection limit |
| Reference example 4 | Boiled | 101.3 | 760 | 24 | Molecular sieve | 17.8 | Below the detection limit |
| Reference example 5 | Boiled | 101.3 | 760 | 24 | Molecular sieve | 18.2 | Below the detection limit |
| Reference example 6 | Boiled | 101.3 | 760 | 24 | Molecular sieve | 1.17 | Below the detection limit |
| Reference example 7 | Boiled | 101.3 | 760 | 24 | Molecular sieve | 11.0 | Many by-product peaks |
| Reference example 8 | Boiled | 101.3 | 760 | 24 | Molecular sieve | 1.54 | Below the detection limit |

As described above, it has especially been confirmed that in the case where $Cs_2O$, $Rb_2O$, $K_2O$ or $Na_2O$ is used as the catalyst in the dehydration reaction according to the present invention, the aromatic nitrile compound is obtained selectively at a high yield.

Example 13

A 5 L 3-necked round-bottom flask was used as a reactor. A magnetic stirrer, the $Cs_2O/SiO_2$ catalyst (10 g (Cs: 5 mmol)), 2-picolinamide (61 g (0.5 mol); produced by Tokyo Chemical Industry Co., Ltd.), and 1,3-dimethoxybenzene (1727 g (12.5 mol); produced by Tokyo Chemical Industry Co., Ltd.) were introduced into the reactor. A reaction distillation device was structured in substantially the same manner as in example 1.

The reaction was performed under the same conditions as in example 2 to obtain a reaction solution containing 38.5 g of 2-cyanopyridine.

The reaction distillation device was used continuously to distill the reaction solution at a pressure of 1.3 kPa to obtain 33.5 g of 2-cyanopyridine. As a result of an analysis performed with FID-GC, the purity thereof was 99.9%.

Example 14

Now, examples of method for producing a carbonate ester using cyanopyridine (carbonate ester generation reaction) will be described. The 2-cyanopyridine obtained in example 13 was used. First, commercially available $CeO_2$ (impurity concentration: 0.02% or lower) was baked at 600° C. for 3 hours in an air atmosphere to obtain a powdery solid catalyst.

A magnetic stirrer, the solid catalyst (0.17 g (1 mmol)), butanol (7.4 g (100 mmol); produced by Wako Pure Chemical Industries, Ltd.), barrel process oil B-28AN (5 g) as the solvent, and 2-cyanopyridine (5.2 g (50 mmol)) were introduced into a 190 mL autoclave (reactor). The air in the autoclave was purged three times with $CO_2$, and then $CO_2$ was introduced into the autoclave such that the pressure would be 5 MPa. The temperature of the autoclave was raised to 132° C. by a band heater and a hot stirrer. The timing when the temperature reached the target temperature was set as the reaction start time. During the reaction, the pressure reached 8 MPa. The reaction was continued for 24 hours at the temperature of the reaction solution of 132° C. as described above. Then, the autoclave was cooled with water. When the autoclave was cooled to room temperature, the pressure in the autoclave was reduced. The solution in the autoclave was diluted two-fold with acetone, and 1-hexanol was added thereto as an internal standard substance. The resultant substance was analyzed with FID-GC. Dibutyl carbonate was obtained in this manner.

Examples 15 Through 47

In examples 15 through 47, a carbonate ester was obtained from an alcohol and $CO_2$ using 2-cyanopyridine under the conditions in which at least one of presence/absence of the solvent, the type of the solvent, the amount of the solvent, the reaction time, the type of the alcohol (substrate), the concentration of the alcohol (substrate), the type of the catalyst, and the amount of the catalyst was different from that in example 14. Specifically, the conditions different from those in example 14 were the type and the amount of the solvent in examples 15 through 18, 41 and 45 through 47 (regarding the solvent, "-" indicates that no solvent was used), the reaction time in examples 18 through 21, 23 through 30, 33 through 39, 43 and 45 through 47, the value of the alcohol/2-cyanopyridine as the materials in examples 23 through 28, 35, 37, 42 and 45 through 47, the amount of the catalyst in examples 25 through 30, 35, 37 and 45 through 47, the type of the catalyst in examples 31 through 34, the temperature of the reaction solution in examples 37 through 47, the reaction pressure in examples 43 and 44, and the type, the amount and the like of the alcohol as the material in examples 35 through 47.

Table 6 below shows the results of the examples of production of the carbonate ester.

TABLE 6

|  | Solvent | Substrate | Substrate amount [mmol] | 2-CP amount [mmol] | Nitrile/ theoretically generated water Molar ratio | Catalyst type | Catalyst amount [mmol] |
| --- | --- | --- | --- | --- | --- | --- | --- |
| Example 14 | High-boiling point solvent barrel process oil (using 5 g of B-28AN) | BuOH | 100 | 50 | 1.0 | $CeO_2$(HSA-20) baked at 600° C. for 3 h | 1.0 |
| Example 15 | High-boiling point solvent barrel process oil (using 15 g of B-28AN) | BuOH | 100 | 50 | 1.0 | $CeO_2$(HSA-20) baked at 600° C. for 3 h | 1.0 |
| Example 16 | High-boiling point solvent barrel process oil (using 5 g of B-30) | BuOH | 100 | 50 | 1.0 | $CeO_2$(HSA-20) baked at 600° C. for 3 h | 1.0 |
| Example 17 | High-boiling point solvent barrel process oil (using 15 g of B-30) | BuOH | 100 | 50 | 1.0 | $CeO_2$(HSA-20) baked at 600° C. for 3 h | 1.0 |
| Example 18 | High-boiling point solvent barrel process oil (using 5 g of B-30) | BuOH | 100 | 50 | 1.0 | $CeO_2$(HSA-20) baked at 600° C. for 3 h | 1.0 |
| Example 19 | — | BuOH | 100 | 50 | 1.0 | $CeO_2$(HSA-20) baked at 600° C. for 3 h | 1.0 |
| Example 20 | — | BuOH | 100 | 50 | 1.0 | $CeO_2$(HSA-20) baked at 600° C. for 3 h | 1.0 |
| Example 21 | — | BuOH | 100 | 50 | 1.0 | $CeO_2$(HSA-20) baked at 600° C. for 3 h | 1.0 |
| Example 22 | — | BuOH | 100 | 50 | 1.0 | $CeO_2$(HSA-20) baked at 600° C. for 3 h | 1.0 |
| Example 23 | — | BuOH | 20 | 100 | 10 | $CeO_2$(HSA-20) baked at 600° C. for 3 h | 1.0 |
| Example 24 | — | BuOH | 100 | 100 | 2.0 | $CeO_2$(HSA-20) baked at 600° C. for 3 h | 1.0 |
| Example 25 | — | BuOH | 200 | 50 | 0.50 | $CeO_2$(HSA-20) baked at 600° C. for 3 h | 0.5 |
| Example 26 | — | BuOH | 300 | 50 | 0.33 | $CeO_2$(HSA-20) baked at 600° C. for 3 h | 0.3 |
| Example 27 | — | BuOH | 20 | 100 | 10 | $CeO_2$(HSA-20) baked at 600° C. for 3 h | 10.0 |
| Example 28 | — | BuOH | 20 | 100 | 10 | $CeO_2$(HSA-20) baked at 600° C. for 3 h | 20.0 |
| Example 29 | — | BuOH | 100 | 50 | 1.0 | $CeO_2$(HSA-20) baked at 600° C. for 3 h | 2.0 |
| Example 30 | — | BuOH | 100 | 50 | 1.0 | $CeO_2$(HSA-20) baked at 600° C. for 3 h | 3.0 |
| Example 31 | — | BuOH | 100 | 50 | 1.0 | $CeO_2$(HSA-5) un-baked | 1.0 |
| Example 32 | — | BuOH | 100 | 50 | 1.0 | $CeO_2$(HSA-5) baked at 600° C. for 3 h | 1.0 |
| Example 33 | — | BuOH | 100 | 50 | 1.0 | $CeO_2$(HSA-5) baked at 600° C. for 3 h | 1.0 |
| Example 34 | — | BuOH | 100 | 50 | 1.0 | $CeO_2$(first rare element) baked at 600° C. for 3 h | 1.0 |
| Example 35 | — | EtOH | 20 | 100 | 10 | $CeO_2$(HSA-20) baked at 600° C. for 3 h | 10.0 |
| Example 36 | — | EtOH | 100 | 50 | 1.0 | $CeO_2$(HSA-20) baked at 600° C. for 3 h | 1.0 |
| Example 37 | — | EtOH | 20 | 100 | 10 | $CeO_2$(HSA-20) baked at 600° C. for 3 h | 10.0 |
| Example 38 | — | EtOH | 100 | 50 | 1.0 | $CeO_2$(HSA-20) baked at 600° C. for 3 h | 1.0 |
| Example 39 | — | EtOH | 100 | 50 | 1.0 | $CeO_2$(HSA-20) baked at 600° C. for 3 h | 1.0 |
| Example 40 | — | EtOH | 100 | 50 | 1.0 | $CeO_2$(HSA-20) baked at 600° C. for 3 h | 1.0 |
| Example 41 | High-boiling point solvent barrel process oil (using 5 g of B-30) | EtOH | 100 | 50 | 1.0 | $CeO_2$(HSA-20) baked at 600° C. for 3 h | 1.0 |
| Example 42 | — | EtOH | 100 | 150 | 3.0 | $CeO_2$(HSA-20) baked at 600° C. for 3 h | 1.0 |
| Example 43 | — | EtOH | 100 | 50 | 1.0 | $CeO_2$(HSA-20) baked at 600° C. for 3 h | 1.0 |
| Example 44 | — | EtOH | 100 | 50 | 1.0 | $CeO_2$(HSA-20) baked at 600° C. for 3 h | 1.0 |
| Example 45 | High-boiling point solvent barrel process oil (using 5 g of B-30) | Ethyleneglycol | 50 | 50 | 1.0 | $CeO_2$(HSA-20) baked at 600° C. for 3 h | 2.0 |
| Example 46 | High-boiling point solvent barrel process oil | 1,2-Propanediol | 50 | 50 | 1.0 | $CeO_2$(HSA-20) baked at 600° C. for 3 h | 2.0 |

TABLE 6-continued

| | | | | | | |
|---|---|---|---|---|---|---|
| Example 47 | (using 5 g of B-30) High-boiling point solvent barrel process oil (using 5 g of B-30) | 1,3-Propanediol | 50 | 50 | 1.0 | CeO$_2$(HSA-20) baked at 600° C. for 3 h | 2.0 |

| | Reaction solution temperature ° C. | Reaction pressure [MPa] | Reaction time [h] | Picolinic acid ester generation amount as by-product mol % | Pyridinimidic acid ester generation amount as by-product mol % | Carbamic acid ester generation amount as by-product mol % | Dialkyl carbonate yield mol % |
|---|---|---|---|---|---|---|---|
| Example 14 | 132 | 8 | 24 | 2.1 | 0.35 | Below the detection limit | 52.5 |
| Example 15 | 132 | 8 | 24 | 1.0 | 0.20 | Below the detection limit | 41.0 |
| Example 16 | 132 | 8 | 24 | 1.7 | 0.30 | Below the detection limit | 55.1 |
| Example 17 | 132 | 8 | 24 | 1.3 | 0.21 | Below the detection limit | 44.5 |
| Example 18 | 132 | 8 | 4 | 0.23 | 0.16 | Below the detection limit | 38.0 |
| Example 19 | 132 | 8 | 4 | 0.35 | 0.14 | Below the detection limit | 46.5 |
| Example 20 | 132 | 8 | 12 | 0.90 | 0.29 | Below the detection limit | 56.7 |
| Example 21 | 132 | 8 | 16 | 1.1 | 0.35 | Below the detection limit | 58.7 |
| Example 22 | 132 | 8 | 24 | 1.8 | 0.44 | Below the detection limit | 63.5 |
| Example 23 | 132 | 8 | 16 | 0.19 | 0.40 | Below the detection limit | 25.0 |
| Example 24 | 132 | 8 | 16 | 1.5 | 0.68 | Below the detection limit | 65.9 |
| Example 25 | 132 | 8 | 16 | 1.8 | 0.16 | Below the detection limit | 45.1 |
| Example 26 | 132 | 8 | 16 | 3.8 | 0.18 | Below the detection limit | 32.5 |
| Example 27 | 132 | 8 | 4 | 0.80 | 0.80 | Below the detection limit | 60.1 |
| Example 28 | 132 | 8 | 4 | 2.0 | 0.70 | Below the detection limit | 72.9 |
| Example 29 | 132 | 8 | 4 | 0.45 | 0.11 | Below the detection limit | 49.8 |
| Example 30 | 132 | 8 | 4 | 0.61 | 0.15 | Below the detection limit | 54.1 |
| Example 31 | 132 | 8 | 24 | 1.8 | 3.1 | Below the detection limit | 33.0 |
| Example 32 | 132 | 8 | 24 | 2.0 | 0.42 | Below the detection limit | 67.1 |
| Example 33 | 132 | 8 | 4 | 0.29 | 0.17 | Below the detection limit | 42.8 |
| Example 34 | 132 | 8 | 4 | 0.19 | 0.15 | Below the detection limit | 35.8 |
| Example 35 | 132 | 8 | 4 | 1.4 | 0.69 | 1.0 | 69.1 |
| Example 36 | 132 | 8 | 4 | 0.51 | 0.14 | 0.41 | 56.8 |
| Example 37 | 120 | 8 | 4 | 0.59 | 0.32 | 0.48 | 66.0 |
| Example 38 | 120 | 8 | 4 | 0.05 | 0.03 | 0.080 | 44.5 |
| Example 39 | 110 | 8 | | 0.03 | 0.01 | Below the detection limit | 33.9 |
| Example 40 | 110 | 8 | 24 | 0.43 | 0.16 | 0.40 | 57.6 |
| Example 41 | 110 | 8 | 24 | 0.28 | 0.49 | 2.2 | 65.0 |
| Example 42 | 110 | 8 | 24 | 0.45 | 0.22 | 0.37 | 63.0 |
| Example 43 | 110 | 1 | 4 | 0.13 | 0.12 | 0.10 | 38.9 |
| Example 44 | 110 | 1 | 24 | 1.9 | 1.6 | 1.7 | 58.5 |
| Example 45 | 130 | 8 | 1 | 0.45 | 0.41 | Below the detection limit | 99.1 |
| Example 46 | 140 | 8 | 1 | 0.40 | 0.20 | Below the detection limit | 99.2 |
| Example 47 | 140 | 8 | 1 | 0.45 | 0.22 | Below the detection limit | 99.0 |

As described above, in examples 14 through 47, it has been confirmed that the carbonate ester is obtained at a high yield within a short reaction time of 24 hours or shorter while the hydration reaction of an aromatic cyano compound with the by-product water was advanced at the same time as the carbonate ester generation reaction.

Example 48

Now, an example of recovery of the catalyst from the carbonate ester reaction solution will be described. The carbonate ester was produced by use of the production device shown in FIG. 1. First, commercially available CeO$_2$ (impurity concentration: 0.02% or lower) was baked at 600° C. for 3 hours in an air atmosphere to obtain a powdery solid catalyst.

The solid catalyst (1.72 g (10 mmol)), butanol (74.1 g (1 mol); produced by Wako Pure Chemical Industries, Ltd.), barrel process oil B-28AN (50 g) as the solvent, and 2-cyanopyridine (52.1 g (0.5 mol)) were introduced into a 1.9 L autoclave (reactor) with a stirrer. The air in the autoclave was purged three times with $CO_2$, and then $CO_2$ was introduced into the autoclave such that the pressure would be 5 MPa. The temperature of the autoclave was raised to 132° C. by a ceramic heater while the substances in the autoclave were stirred. The timing when the temperature reached the target temperature was set as the reaction start time. During the reaction, the pressure reached 8 MPa.

The reaction was continued for 24 hours at the temperature of the reaction solution of 132° C. as described above. Then, the pressure in the autoclave was returned to the atmospheric pressure. The reaction solution was introduced to a middle portion of a distillation column having a reduced pressure of 2.7 kPa, and simple distillation was performed. From the top of the distillation column, a mixture of BuOH, dibutyl carbonate, 2-cyanopyridine and 2-picolinamide was recovered. From the bottom of the distillation column, the catalyst and barrel process oil were recovered.

The catalyst and the solvent recovered above, butanol (74.1 g (1 mol); produced by Wako Pure Chemical Industries, Ltd.), and 2-cyanopyridine (52.1 g (0.5 mol)) were introduced into a 1.9 L autoclave (reactor) with a stirrer. The air in the autoclave was purged three times with $CO_2$, and then $CO_2$ was introduced into the autoclave such that the pressure would be 5 MPa. The temperature of the autoclave was raised to 132° C. by a ceramic heater while the substances in the autoclave were stirred. The timing when the temperature reached the target temperature was set as the reaction start time. During the reaction, the pressure reached 8 MPa. After the reaction was continued for 24' hours, the autoclave was cooled with water. When the autoclave was cooled to room temperature, the pressure in the autoclave was reduced, and a part of the reaction solution was sampled. The sampled reaction solution was diluted twofold with acetone, and 1-hexanol was added thereto as an internal standard substance. The resultant substance was analyzed with FID-GC. As a result, the yield of dibutyl carbonate was 54 mol %.

Then, the reaction solution was distilled in the order shown in FIG. 1 to obtain 40 g of dibutyl carbonate. An analysis with FID-GC showed that the purity was 99.9%.

As can be seen, it has been confirmed that even in the case where the catalyst once used is recovered and used again for the carbonate ester generation reaction, the carbonate ester is obtained at a high yield.

As described above, it has been confirmed that also in the carbonate ester generation reaction, in the case where a solvent having a boiling point higher than that of aromatic carboamide is used, the components may be separated from each other merely by distillation with no need of the step of solid-liquid separation of the catalyst. Thus, an efficient process is realized.

Preferable embodiments of the present invention have been described above in detail with reference to the attached drawings. The present invention is not limited to any of the embodiments. A person of ordinary skill in the art of the present invention would obviously conceive any of various altered or modified examples within the technological scope defined by the claims, and such altered or modified examples are construed as being duly encompassed in the technological scope of the present invention.

REFERENCE SIGNS LIST

1 Carbonate ester reactor
2 Catalyst separation column
3 Dehydration agent separation column
4. Amide separation column
5 Carbonate ester recovery column
6 Nitrile regeneration reactor
7 Water separation column
8 Decompression pump

The invention claimed is:

1. A method for producing an aromatic nitrile compound, comprising:
a dehydration reaction of dehydrating an aromatic amide compound;
wherein the dehydration reaction uses a solvent comprising one or a plurality of substances selected from 1,2-dimethoxybenzene, 1,3-dimethoxybenzene and 1,3,5-trimethoxybenzene.

2. The method for producing an aromatic nitrile compound according to claim 1, wherein a total amount of the one or the plurality of substances selected from 1,2-dimethoxybenzene, 1,3-dimethoxybenzene and 1,3,5-trimethoxybenzene is 5% by weight or greater with respect to the solvent.

3. The method for producing an aromatic nitrile compound according to claim 1, wherein the solvent is formed of only the one or the plurality of substances selected from 1,2-dimethoxybenzene, 1,3-dimethoxybenzene and 1,3,5-trimethoxybenzene.

4. The method for producing an aromatic nitrile compound according to claim 1, wherein the solvent is a mixed solvent further comprising a compound having a boiling point that is higher than the boiling point of the aromatic nitrile compound and the boiling point of water and is lower than the boiling point of the aromatic amide compound.

5. The method for producing an aromatic nitrile compound according to claim 1, wherein the solvent is used in an amount larger than, or equal to, an equimolecular amount of the aromatic amide compound.

6. The method for producing an aromatic nitrile compound according to claim 1, wherein the dehydration reaction is performed in a state where the solvent is boiled.

7. The method for producing an aromatic nitrile compound according to claim 1, wherein the dehydration reaction is performed under the condition of normal pressure or a reduced pressure.

8. The method for producing an aromatic nitrile compound according to claim 1, wherein a reaction solution of the dehydration reaction has a temperature of 170° C. or higher and lower than 230° C.

9. The method for producing an aromatic nitrile compound according to claim 1, wherein the aromatic amide compound comprises pyridine carboamide, and the aromatic nitrile compound comprises cyanopyridine.

10. The method for producing an aromatic nitrile compound according to claim 1, wherein the dehydration reaction uses a catalyst comprising cesium.

11. A method for producing a carbonate ester, comprising:
a first reaction step including a carbonate ester generation reaction of reacting an alcohol and carbon dioxide in the presence of an aromatic nitrile compound to generate a carbonate ester and water, and a hydration reaction of hydrating the aromatic nitrile compound with the generated water to generate an aromatic amide compound; and a second reaction step of, after the aromatic amide compound is separated from a reaction system of the first reaction step, regenerating the aromatic amide compound into an aromatic nitrile compound by a dehydration reaction of dehydrating the aromatic amide compound in a solvent comprising one or a plurality of substances selected from 1,2-dimethoxybenzene, 1,3-dimethoxybenzene and 1,3,5-trimethoxybenzene;

wherein at least a part of the aromatic nitrile compound regenerated in the second reaction step is used in the first reaction step.

12. The method for producing a carbonate ester according to claim 11, wherein a total amount of the one or the plurality of substances selected from 1,2-dimethoxybenzene, 1,3-dimethoxybenzene and 1,3,5-trimethoxybenzene is 5% by weight or greater with respect to the solvent.

13. The method for producing an aromatic nitrile compound according to claim 11, wherein the solvent is formed of only the one or the plurality of substances selected from 1,2-dimethoxybenzene, 1,3-dimethoxybenzene and 1,3,5-trimethoxybenzene.

14. The method for producing a carbonate ester according to claim 11, wherein the solvent is a mixed solvent further comprising a compound having a boiling point that is higher than the boiling point of the aromatic nitrile compound and the boiling point of water and is lower than the boiling point of the aromatic amide compound.

15. The method for producing a carbonate ester according to claim 11, wherein the solvent is used in an amount larger than, or equal to, an equimolecular amount of the aromatic amide compound.

16. The method for producing a carbonate ester according to claim 11, wherein the dehydration reaction is performed in a state where the solvent is boiled.

17. The method for producing a carbonate ester according to claim 11, wherein the dehydration reaction is performed under the condition of normal pressure or a reduced pressure.

18. The method for producing a carbonate ester according to claim 11, wherein a reaction solution of the dehydration reaction has a temperature of 170° C. or higher and lower than 230° C.

19. The method for producing a carbonate ester according to claim 11, wherein the aromatic amide compound comprises pyridine carboamide, and the aromatic nitrile compound comprises cyanopyridine.

20. The method for producing a carbonate ester according to claim 11, wherein the dehydration reaction uses a catalyst comprising cesium.

21. The method for producing a carbonate ester according to claim 11, wherein the carbonate ester generation reaction uses a catalyst comprising cerium.

22. The method for producing a carbonate ester according to claim 11, wherein the alcohol comprises an alcohol having a carbon number of 1 to 6.

* * * * *